(12) United States Patent
Amin et al.

(10) Patent No.: US 9,073,819 B2
(45) Date of Patent: Jul. 7, 2015

(54) COMPOSITIONS, METHODS OF USE, AND METHODS OF TREATMENT

(75) Inventors: Jahanshah Amin, Temple Terrace, FL (US); Kirpal S. Bisht, Tampa, FL (US); Meghanath Gali, Houston, TX (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/128,310

(22) PCT Filed: Jun. 29, 2012

(86) PCT No.: PCT/US2012/044808
§ 371 (c)(1),
(2), (4) Date: Apr. 15, 2014

(87) PCT Pub. No.: WO2013/003669
PCT Pub. Date: Jan. 3, 2013

(65) Prior Publication Data
US 2014/0221473 A1      Aug. 7, 2014

Related U.S. Application Data

(60) Provisional application No. 61/503,024, filed on Jun. 30, 2011.

(51) Int. Cl.
| A61K 31/357 | (2006.01) |
| C07C 215/44 | (2006.01) |
| C07D 317/72 | (2006.01) |
| C07C 211/40 | (2006.01) |
| C07C 217/52 | (2006.01) |
| C07C 325/02 | (2006.01) |
| C07C 251/20 | (2006.01) |
| C07C 251/44 | (2006.01) |
| C07C 323/30 | (2006.01) |

(52) U.S. Cl.
CPC ............ *C07C 215/44* (2013.01); *C07D 317/72* (2013.01); *C07C 211/40* (2013.01); *C07C 217/52* (2013.01); *C07C 325/02* (2013.01); *C07C 251/20* (2013.01); *C07C 251/44* (2013.01); *C07C 2101/14* (2013.01); *C07C 323/30* (2013.01)

(58) Field of Classification Search
CPC .................................................... C07C 215/44
USPC ......................................................... 514/462
See application file for complete search history.

(56) References Cited

U.S. PATENT DOCUMENTS

| 5,384,331 A | 1/1995 | Kogan |
| 2009/0246255 A1 | 10/2009 | Meyer |

FOREIGN PATENT DOCUMENTS

| WO | 2004028522 | 4/2004 |
| WO | 2007111880 | 10/2007 |

OTHER PUBLICATIONS

Yokoyama et al., Tetrehed. (2009), vol. 65(27), pp. 5181-5191.*
Yokoyama et al., Bull. Chem. Soc. of Japan, (2009), vol. 82(12), pp. 1528-2531.*
King, Med. Chem. Principle and Practice (1994), pp. 206-208.*
Paola Zarantonello, et al., Novel analogues of ketamine and phencyclidine as NMDA receptor antagonist. Bioorganic & Medicinal Chemistry Letters. Apr. 2011, 21 (7), pp. 2059-2063.
International Search Report and Written Opinion mailed Jan. 30, 2013.

* cited by examiner

*Primary Examiner* — Taofiq A Solola
(74) *Attorney, Agent, or Firm* — Thomas Horstemeyer, LLP

(57) ABSTRACT

Embodiments of the present disclosure provide compositions including ketamine analogs, salts, and disalts, pharmaceutical compositions including ketamine analogs, salts, or disalts, methods of treatment of a condition or disease, methods of treatment using compositions or pharmaceutical compositions, and the like.

20 Claims, 28 Drawing Sheets

| Saline | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA53 | 28 | 0 | 0 | 5 | 26 | 0 | 0 | 0 | 0 | 3 | 3 | 1 | 0 |
| JA54 | 24 | 0 | 0 | 3 | 21 | 1 | 1 | 0 | 0 | 0 | 0 | 0 | 0 |
| JA67 | 49 | 1 | 0 | 2 | 45 | 1 | 1 | 0 | 0 | 0 | 0 | 0 | 0 |
| JA68 | 37 | 0 | 0 | 1 | 48 | 2 | 2 | 0 | 0 | 2 | 2 | 1 | 0 |
| JA81 | 32 | 0 | 0 | 2 | 38 | 1 | 1 | 0 | 0 | 0 | 0 | 0 | 0 |
| JA82 | 4 | 0 | 0 | 0 | 46 | 0 | 0 | 0 | 0 | 7 | 29 | 0 | 0 |
| Mean | 29.00 | 0.17 | 0.00 | 2.17 | 37.33 | 0.83 | 0.83 | 0.00 | 0.00 | 2.00 | 5.17 | 0.00 | 0.00 |
| S.D. | 14.99 | 0.41 | 0.00 | 1.72 | 11.34 | 0.75 | 0.75 | 0.00 | 0.00 | 2.76 | 11.69 | 0.00 | 0.00 |
| SEM | 6.121 | 0.167 | 0 | 0.703167 | 4.6308 | 0.30732 | 0.30732 | 0 | 0 | 1.1254629 | 4.7708606 | 0 | 0 |

| 1mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA55 | 31 | 0 | 0 | 0 | 55 | 0 | 0 | 0 | 0 | 0 | 0 | 0 | 0 |
| JA56 | 30 | 0 | 0 | 2 | 55 | 1 | 1 | 0 | 0 | 7 | 16 | 0 | 0 |
| JA79 | 14 | 0 | 0 | 3 | 31 | 0 | 0 | 0 | 0 | 6 | 19 | 0 | 0 |
| JA80 | 41 | 0 | 0 | 1 | 54 | 2 | 2 | 0 | 0 | 0 | 0 | 0 | 0 |
| JA83 | 39 | 0 | 0 | 6 | 43 | 2 | 2 | 0 | 0 | 4 | 4 | 0 | 0 |
| JA84 | 32 | 0 | 0 | 1 | 44 | 0 | 0 | 0 | 0 | 0 | 0 | 0 | 0 |
| Mean | 31.17 | 0.00 | 0.00 | 2.17 | 47.00 | 1.00 | 1.00 | 0.00 | 0.00 | 2.83 | 6.50 | 0.00 | 0.00 |
| S.D. | 9.54 | 0.00 | 0.00 | 2.14 | 9.57 | 0.89 | 0.89 | 0.00 | 0.00 | 3.25 | 8.71 | 0.00 | 0.00 |
| SEM | 3.8937 | 0 | 0 | 0.872417 | 3.9073 | 0.36515 | 0.36515 | 0 | 0 | 1.3270686 | 3.5566838 | 0 | 0 |

| 3mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA65 | 13 | 0 | 0 | 1 | 38 | 0 | 0 | 0 | 0 | 24 | 24 | 39 | 0 |
| JA66 | 7 | 0 | 0 | 0 | 28 | 0 | 0 | 0 | 0 | 6 | 6 | 8 | 0 |
| JA69 | 25 | 0 | 0 | 2 | 6 | 0 | 0 | 0 | 0 | 2 | 2 | 1 | 0 |
| JA70 | 10 | 0 | 0 | 0 | 31 | 3 | 3 | 0 | 0 | 19 | 19 | 62 | 0 |
| JA85 | 13 | 0 | 0 | 0 | 1 | 1 | 1 | 0 | 0 | 11 | 11 | 21 | 0 |
| JA86 | 29 | 0 | 0 | 1 | 42 | 1 | 1 | 0 | 0 | 0 | 0 | 0 | 0 |
| Mean | 16.17 | 0.00 | 0.00 | 0.67 | 24.33 | 0.83 | 0.83 | 0.00 | 0.00 | 10.33 | 21.83 | 0.00 | 0.00 |
| S.D. | 8.77 | 0.00 | 0.00 | 0.82 | 16.95 | 1.17 | 1.17 | 0.00 | 0.00 | 9.56 | 24.54 | 0.00 | 0.00 |
| SEM | 3.5816 | 0 | 0 | 0.333333 | 6.9218 | 0.47726 | 0.47726 | 0 | 0 | 3.9044135 | 10.018039 | 0 | 0 |

FIG. 22 A

| 10mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA59 | 20 | 0 | 0 | 0 | 47 | 5 | 0 | 0 | 0 | 9 | 14 | 0 | 0 |
| JA60 | 5 | 0 | 0 | 1 | 49 | 2 | 0 | 0 | 0 | 8 | 15 | 0 | 0 |
| JA73 | 14 | 1 | 0 | 4 | 39 | 2 | 0 | 0 | 0 | 18 | 50 | 0 | 0 |
| JA74 | 1 | 4 | 0 | 3 | 44 | 4 | 0 | 0 | 0 | 22 | 115 | 0 | 0 |
| JA87 | 13 | 0 | 0 | 3 | 43 | 0 | 0 | 0 | 0 | 0 | 0 | 0 | 0 |
| JA88 | 2 | 1 | 1 | 1 | 22 | 3 | 0 | 0 | 0 | 22 | 211 | 0 | 0 |
| Mean | 9.17 | 1.00 | 0.17 | 2.00 | 40.67 | 2.67 | 0.00 | 0.00 | 0.00 | 13.17 | 67.50 | 0.00 | 0.00 |
| S.D. | 7.63 | 1.55 | 0.41 | 1.55 | 9.77 | 1.75 | 0.00 | 0.00 | 0.00 | 8.91 | 81.64 | 0.00 | 0.00 |
| SEM | 3.1136 | 0.632 | 0.1666667 | 0.632456 | 3.9889 | 0.71492 | 0 | 0 | 0 | 3.6370012 | 33.331417 | 0 | 0 |

| 20mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA61 | 4 | 0 | 0 | 1 | 44 | 0 | 0 | 0 | 0 | 18 | 55 | 0 | 0 |
| JA62 | 4 | 0 | 0 | 0 | 51 | 6 | 0 | 0 | 0 | 6 | 16 | 0 | 0 |
| JA76 | 5 | 0 | 0 | 3 | 32 | 0 | 0 | 0 | 0 | 23 | 75 | 0 | 0 |
| JA89 | 0 | 0 | 0 | 0 | 24 | 0 | 0 | 0 | 0 | 8 | 106 | 0 | 0 |
| JA90 | 24 | 0 | 0 | 0 | 30 | 0 | 0 | 0 | 0 | 0 | 0 | 0 | 0 |
| JA92 | 0 | 0 | 0 | 0 | 31 | 3 | 0 | 0 | 0 | 10 | 138 | 0 | 0 |
| Mean | 6.17 | 0.00 | 0.00 | 0.67 | 35.33 | 0.50 | 0.00 | 0.00 | 0.00 | 10.83 | 65.00 | 0.00 | 0.00 |
| S.D. | 9.00 | 0.00 | 0.00 | 1.21 | 10.07 | 1.22 | 0.00 | 0.00 | 0.00 | 8.35 | 52.60 | 0.00 | 0.00 |
| SEM | 3.6735 | 0 | 0 | 0.494413 | 4.1123 | 0.5 | 0 | 0 | 0 | 3.4099528 | 21.475568 | 0 | 0 |

| 50mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA64 | 0 | 9 | 2 | 0 | 46 | 5 | 0 | 0 | 0 | 4 | 10 | 17 | 66 |
| JA77 | 0 | 17 | 1 | 0 | 36 | 6 | 1 | 1 | 0 | 0 | 0 | 14 | 33 |
| JA78 | 6 | 6 | 0 | 0 | 38 | 0 | 0 | 0 | 0 | 15 | 90 | 10 | 11 |
| JA91 | 0 | 26 | 6 | 0 | 0 | 8 | 1 | 1 | 0 | 0 | 0 | 29 | 226 |
| Mean | 1.50 | 14.50 | 2.25 | 0.00 | 30.00 | 4.75 | 0.50 | 0.50 | 0.00 | 4.75 | 25.00 | 17.50 | 84.00 |
| S.D. | 3.00 | 8.96 | 2.63 | 0.00 | 20.46 | 3.40 | 0.58 | 0.58 | 0.00 | 7.09 | 43.59 | 8.19 | 97.33 |
| SEM | 1.5 | 4.481 | 1.3149778 | 0 | 10.231 | 1.70171 | 0.2887 | 0.2887 | 0 | 3.5443617 | 21.794495 | 4.092676 | 48.66381 |

FIG. 22 B

| 100mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA57 | 0 | 0 | 0 | 0 | 38 | 14 | 29 | 1 | 1 | 0 | 0 | 10 | 129 |
| JA58 | 0 | 0 | 2 | 0 | 15 | 10 | 50 | 6 | 52 | 0 | 0 | 6 | 8 |
| JA71 | 0 | 1 | 2 | 0 | 3 | 0 | 2 | 11 | 285 | 0 | 0 | 0 | 0 |
| JA72 | 1 | 43 | 1 | 0 | 70 | 29 | 1 | 0 | 0 | 0 | 0 | 15 | 210 |
| Mean | 0.25 | 11.00 | 1.25 | 0.00 | 31.50 | 13.25 | 20.50 | 4.50 | 84.50 | 0.00 | 0.00 | 7.75 | 86.75 |
| S.D. | 0.50 | 21.34 | 0.96 | 0.00 | 29.49 | 12.04 | 23.56 | 5.07 | 135.85 | 0.00 | 0.00 | 6.34 | 101.16 |
| SEM | 0.25 | 10.67 | 0.4787136 | 0 | 14.745 | 6.01907 | 11.779 | 2.533114 | 67.927 | 0 | 0 | 3.172144 | 50.58224 |

FIG. 22 C

| Saline | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA53 | 43 | 0 | 0 | 9 | 45 | 0 | 0 | 0 | 0 | 0 | 0 | 0 | 0 |
| JA54 | 44 | 1 | 0 | 7 | 57 | 8 | 0 | 0 | 0 | 2 | 63 | 0 | 0 |
| JA67 | 76 | 1 | 0 | 2 | 94 | 4 | 0 | 0 | 0 | 2 | 2 | 0 | 0 |
| JA68 | 65 | 0 | 0 | 1 | 82 | 4 | 0 | 0 | 0 | 3 | 0 | 0 | 0 |
| JA81 | 48 | 0 | 0 | 2 | 77 | 1 | 0 | 0 | 0 | 0 | 2 | 0 | 0 |
| JA82 | 5 | 0 | 0 | 0 | 104 | 0 | 0 | 0 | 0 | 15 | 245 | 0 | 0 |
| Mean | 46.83 | 0.17 | 0.00 | 3.50 | 76.50 | 2.83 | 0.00 | 0.00 | 0.00 | 5.00 | 52.00 | 0.00 | 0.00 |
| S.D. | 24.31 | 0.41 | 0.00 | 3.62 | 22.21 | 3.13 | 0.00 | 0.00 | 0.00 | 6.13 | 97.75 | 0.00 | 0.00 |
| SEM | 9.9244 | 0.167 | 0 | 1.477611 | 9.0655 | 1.2758 | 0 | 0 | 0 | 2.503331 | 39.907393 | 0 | 0 |

| 1mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA55 | 59 | 0 | 0 | 3 | 102 | 0 | 0 | 0 | 0 | 1 | 2 | 0 | 0 |
| JA56 | 65 | 0 | 0 | 4 | 97 | 3 | 0 | 0 | 0 | 14 | 36 | 0 | 0 |
| JA79 | 37 | 0 | 0 | 4 | 55 | 1 | 0 | 0 | 0 | 7 | 23 | 0 | 0 |
| JA80 | 75 | 0 | 0 | 3 | 97 | 2 | 0 | 0 | 0 | 0 | 0 | 0 | 0 |
| JA83 | 62 | 0 | 0 | 7 | 81 | 7 | 0 | 0 | 0 | 6 | 12 | 0 | 0 |
| JA84 | 60 | 0 | 0 | 3 | 73 | 0 | 0 | 0 | 0 | 0 | 0 | 0 | 0 |
| Mean | 59.67 | 0.00 | 0.00 | 4.00 | 84.17 | 2.17 | 0.00 | 0.00 | 0.00 | 4.67 | 12.17 | 0.00 | 0.00 |
| S.D. | 12.52 | 0.00 | 0.00 | 1.55 | 18.07 | 2.64 | 0.00 | 0.00 | 0.00 | 5.50 | 14.73 | 0.00 | 0.00 |
| SEM | 5.1099 | 0 | 0 | 0.632456 | 7.3775 | 1.0775 | 0 | 0 | 0 | 2.245984 | 6.0134109 | 0 | 0 |

| 3mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA65 | 22 | 0 | 0 | 4 | 70 | 0 | 0 | 0 | 0 | 34 | 60 | 0 | 0 |
| JA66 | 23 | 0 | 0 | 0 | 48 | 1 | 0 | 0 | 0 | 15 | 36 | 0 | 0 |
| JA69 | 41 | 0 | 0 | 7 | 17 | 3 | 0 | 0 | 0 | 4 | 3 | 0 | 0 |
| JA70 | 31 | 0 | 0 | 3 | 56 | 4 | 0 | 0 | 0 | 23 | 70 | 0 | 0 |
| JA85 | 29 | 0 | 0 | 1 | 17 | 1 | 0 | 0 | 0 | 16 | 42 | 0 | 0 |
| JA86 | 58 | 0 | 0 | 4 | 83 | 5 | 0 | 0 | 0 | 2 | 1 | 0 | 0 |
| Mean | 34.00 | 0.00 | 0.00 | 3.17 | 48.50 | 2.00 | 0.00 | 0.00 | 0.00 | 15.67 | 35.33 | 0.00 | 0.00 |
| S.D. | 13.59 | 0.00 | 0.00 | 2.48 | 27.18 | 2.00 | 0.00 | 0.00 | 0.00 | 11.94 | 28.56 | 0.00 | 0.00 |
| SEM | 5.5498 | 0 | 0 | 1.013794 | 11.096 | 0.8165 | 0 | 0 | 0 | 4.876246 | 11.660951 | 0 | 0 |

FIG. 23 A

| 10mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA59 | 35 | 0 | 0 | 6 | 75 | 7 | 0 | 0 | 0 | 22 | 40 | 0 | 0 |
| JA60 | 19 | 0 | 0 | 3 | 90 | 5 | 0 | 0 | 0 | 23 | 62 | 0 | 0 |
| JA73 | 26 | 1 | 0 | 7 | 69 | 3 | 0 | 0 | 0 | 24 | 60 | 0 | 0 |
| JA74 | 9 | 4 | 0 | 4 | 94 | 5 | 0 | 0 | 0 | 42 | 179 | 0 | 0 |
| JA87 | 27 | 0 | 0 | 3 | 80 | 0 | 0 | 0 | 0 | 5 | 6 | 0 | 0 |
| JA88 | 3 | 1 | 1 | 3 | 29 | 3 | 0 | 0 | 0 | 35 | 498 | 0 | 0 |
| Mean | 19.83 | 1.00 | 0.17 | 4.33 | 72.83 | 3.83 | 0.00 | 0.00 | 0.00 | 25.17 | 140.83 | 0.00 | 0.00 |
| S.D. | 12.01 | 1.55 | 0.41 | 1.75 | 23.39 | 2.40 | 0.00 | 0.00 | 0.00 | 12.67 | 184.46 | 0.00 | 0.00 |
| SEM | 4.9018 | 0.632 | 0.166667 | 0.71492 | 9.5478 | 0.9804 | 0 | 0 | 0 | 5.173114 | 75.304013 | 0 | 0 |

| 20mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA61 | 11 | 0 | 0 | 2 | 74 | 0 | 0 | 0 | 0 | 41 | 164 | 0 | 0 |
| JA62 | 6 | 0 | 0 | 2 | 93 | 6 | 0 | 0 | 0 | 20 | 62 | 0 | 0 |
| JA76 | 9 | 1 | 0 | 5 | 55 | 2 | 0 | 0 | 0 | 42 | 137 | 0 | 0 |
| JA89 | 0 | 0 | 0 | 3 | 39 | 1 | 1 | 0 | 0 | 1 | 0 | 0 | 0 |
| JA90 | 51 | 0 | 0 | 4 | 61 | 0 | 3 | 0 | 0 | 1 | 0 | 0 | 0 |
| JA92 | 0 | 0 | 0 | 1 | 47 | 3 | 3 | 0 | 0 | 30 | 295 | 0 | 0 |
| Mean | 12.83 | 0.00 | 0.00 | 2.83 | 61.50 | 1.17 | 1.17 | 0.00 | 0.00 | 22.50 | 109.67 | 0.00 | 0.00 |
| S.D. | 19.24 | 0.00 | 0.00 | 1.47 | 19.53 | 1.17 | 1.17 | 0.00 | 0.00 | 18.49 | 113.47 | 0.00 | 0.00 |
| SEM | 7.8546 | 0 | 0 | 0.600925 | 7.9739 | 0.4773 | 0.4787 | 0 | 0 | 7.548731 | 46.322541 | 0 | 0 |

| 50mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA64 | 0 | 11 | 2 | 1 | 81 | 5 | 0 | 0 | 0 | 17 | 43 | 29 | 90 |
| JA77 | 2 | 32 | 8 | 2 | 72 | 10 | 2 | 0 | 0 | 0 | 0 | 21 | 39 |
| JA78 | 6 | 6 | 0 | 1 | 56 | 0 | 0 | 0 | 0 | 21 | 410 | 10 | 11 |
| JA91 | 0 | 32 | 8 | 0 | 0 | 10 | 1 | 0 | 0 | 0 | 0 | 50 | 471 |
| Mean | 2.00 | 20.25 | 4.50 | 1.00 | 52.25 | 6.25 | 0.75 | 0.00 | 0.00 | 9.50 | 113.25 | 27.50 | 152.75 |
| S.D. | 2.83 | 13.72 | 4.12 | 0.82 | 36.34 | 4.79 | 0.96 | 0.00 | 0.00 | 11.09 | 198.87 | 16.90 | 214.67 |
| SEM | 1.4142 | 6.86 | 2.061553 | 0.408248 | 18.168 | 2.3936 | 0.4787 | 0 | 0 | 5.545268 | 99.434547 | 8.450838 | 107.3362 |

FIG. 23 B

| 100mg/kg | Rearing | Sway | Backward Movement | Grooming | Sniffing | Circling | Fall | Loss of Posture (freq) | Loss of Posture (time) | Immobility (freq) | Immobility (time) | Unsteady Gait (freq) | Unsteady Gait (time) |
|---|---|---|---|---|---|---|---|---|---|---|---|---|---|
| JA57 | 0 | 17 | 3 | 0 | 88 | 27 | 43 | 1 | 1 | 0 | 0 | 28 | 319 |
| JA58 | 0 | 14 | 4 | 0 | 51 | 33 | 88 | 7 | 60 | 0 | 0 | 7 | 10 |
| JA71 | 0 | 4 | 8 | 0 | 15 | 1 | 21 | 13 | 291 | 0 | 0 | 6 | 11 |
| JA72 | 1 | 65 | 5 | 0 | 130 | 48 | 1 | 0 | 0 | 6 | 42 | 22 | 336 |
| Mean | 0.25 | 25.00 | 5.00 | 0.00 | 71.00 | 27.25 | 38.25 | 5.25 | 88.00 | 1.50 | 10.50 | 15.75 | 169.00 |
| S.D. | 0.50 | 27.24 | 2.16 | 0.00 | 49.35 | 19.60 | 37.34 | 6.02 | 138.21 | 3.00 | 21.00 | 10.97 | 183.15 |
| SEM | 0.25 | 13.62 | 1.080123 | 0 | 24.675 | 9.8011 | 18.67 | 3.0104 | 69.105 | 1.5 | 10.5 | 5.482928 | 91.57602 |

FIG. 23 C

Parameters obtained from fitting the logistic equation to concentration-response relationship data points for ketamine, Oxime monosalt, and Oxime disalt

| NMDA subtype | $IC_{50}$ (μM) | Slope | Extrapolated Minimum | n |
|---|---|---|---|---|
| NR1/NR2A | | | | |
| Ketamine | 1.86 ± 0.40 | 1.39 ± 0.13 | 0.09 ± 0.06 | 5 |
| Oxime monosalt | 6.06 ± 0.67 | 1.03 ± 0.10 | 0.06 ± 0.01 | 5 |
| Oxime disalt | 1.88 ± 0.44 | 0.83 ± 0.06 | 0.08 ± 0.03 | 6 |
| NR1/NR2B | | | | |
| Ketamine | 1.21 ± 0.42 | 1.12 ± 0.13 | 0.15 ± 0.02 | 4 |
| Oxime monosalt | 1.09 ± 0.11 | 0.93 ± 0.02 | 0.06 ± 0.003 | 6 |
| Oxime disalt | 1.22 ± 0.34 | 0.93 ± 0.04 | 0.11 ± 0.04 | 4 |
| NR1/NR2C | | | | |
| Ketamine | 0.34 ± 0.07 | 0.86 ± 0.06 | 0.10 ± 0.02 | 3 |
| Oxime monosalt | 0.78 ± 0.10 | 0.88 ± 0.01 | 0.09 ± 0.02 | 6 |
| Oxime disalt | 0.52 ± 0.07 | 0.77 ± 0.04 | 0.09 ± 0.01 | 4 |
| NR1/NR2D | | | | |
| Ketamine | 0.80 ± 0.10 | 0.99 ± 0.06 | 0.10 ± 0.03 | 4 |
| Oxime monosalt | 3.83 ± 0.48 | 0.95 ± 0.03 | 0.09 ± 0.01 | 4 |
| Oxime disalt | 2.87 ± 0.26 | 0.91 ± 0.01 | 0.08 ± 0.03 | 5 |

FIG. 25

COMPOSITIONS, METHODS OF USE, AND METHODS OF TREATMENT

CROSS-REFERENCE TO RELATED APPLICATION

This application is the 35 U.S.C. §371 national stage of, and claims priority to and the benefit of, PCT application PCT/US2012/044808, filed Jun. 29, 2012, which claims priority to and the benefit of U.S. Provisional Application No. 61/503,024, filed on Jun. 30, 2011, herein incorporated by reference in its entirety.

BACKGROUND

The cerebellum is a region of brain positioned below cerebral cortex. It is approximately 10% of the brain by volume, but its main cells, namely granule neurons, are more numerous than all of the neurons in the rest of the brain combined. The cerebellum has a primary role in motor control and learning, but appears to participate in higher cognitive functions like attention and language, as well as in emotions such as fear and pleasure. A prevailing hypothesis states that the cerebellum is, in principle, a sensory structure. In motor-related activity, it adjusts and fine-tunes motor activities in response to sensory inputs. Likewise, the cerebellum may also play an important role in coordinating cognitive tasks. Although the cerebellum contribution to mental disease and cognitive function has been shown, this important structure of the brain has never been utilized as a target for therapeutic agents.

The $\alpha 6\beta 2/3\delta$ receptors are subtypes of the $GABA_A$ receptor family abundantly and exclusively expressed within the granule neurons of the cerebellum; the most abundant neurons within the CNS. $GABA_A$ receptors are the main target of most anesthetics, but there was little evidence that phencyclidine (PCP) or ketamine affect these receptors. We have shown that at clinically relevant concentrations, in vitro and in situ, ketamine, but not PCP, selectively modulates $\alpha 6\beta 2\delta$ and $\alpha 6\beta 3\delta$ $GABA_A$ receptors. These data suggest that the selection of ketamine from among 200 different PCP different analogues for clinical use may be due to its selective actions on $\alpha 6\beta 2/3\delta$ receptors within the cerebellum. Given the abundance of the granule neurons, even a minute increase in the activity of $\alpha 6\beta 2/3\delta$ $GABA_A$ receptors by ketamine can potentially impact the excitability of the granule neurons and thus transmission of information through the cerebellum. However, ketamine has side effects such as vivid dreams, illusions, disruptions of cognitive function, mood changes. Thus, alternatives to ketamine are desired.

SUMMARY

Embodiments of the present disclosure provide compositions including ketamine analogues, salts, and disalts, pharmaceutical compositions including ketamine analogues, salts, or disalts, methods of treatment of a condition or disease, methods of treatment using compositions or pharmaceutical compositions, and the like.

An embodiment of the composition, among others, includes: a ketamine analogue having one of the following structures:

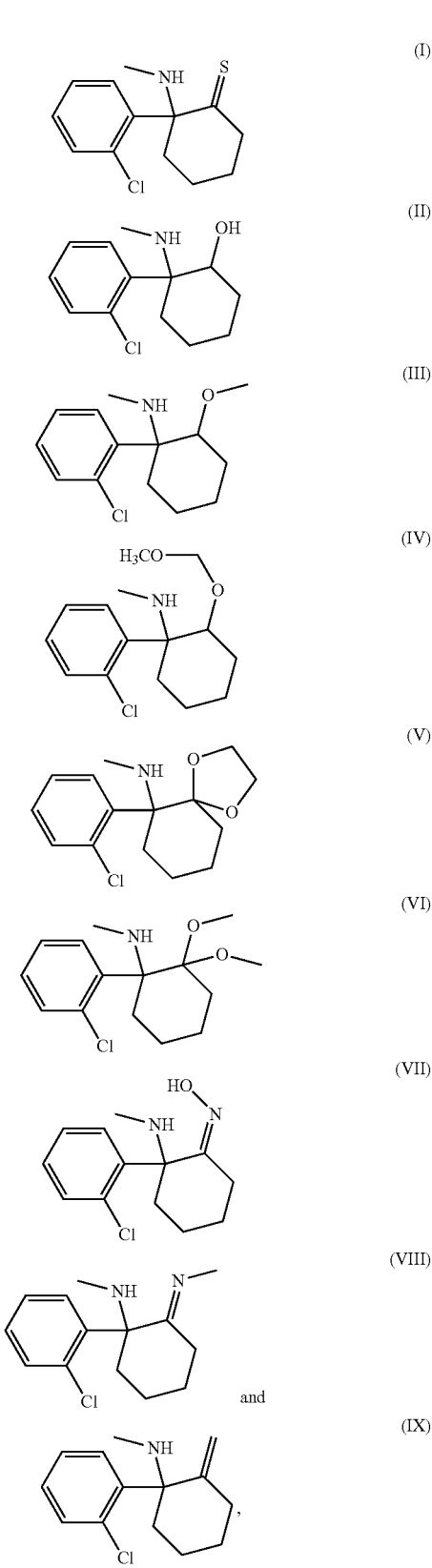

a salt thereof, or a disalt thereof

An embodiment of the pharmaceutical composition, among others, includes: a therapeutically effective amount of a ketamine analogue as described herein, a pharmaceutically acceptable salt thereof, or a pharmaceutically acceptable disalt thereof, and a pharmaceutically acceptable carrier, to treat a condition.

An embodiment of the method of treating a condition, among others, includes: delivering to a subject in need thereof, a pharmaceutical composition, wherein the pharmaceutical composition includes a therapeutically effective amount of a ketamine analogue as described herein, a pharmaceutically acceptable salt thereof, or a pharmaceutically acceptable disalt thereof, and a pharmaceutically acceptable carrier, to treat a condition.

An embodiment of the method of increasing GABAA receptor activity while retaining the blocking action on the NMDA receptors, relative to phencyclidine, among others, includes: delivering to a subject in need thereof, a pharmaceutical composition, wherein the pharmaceutical composition includes a therapeutically effective amount of a ketamine analogue as described herein, a pharmaceutically acceptable salt thereof, or a pharmaceutically acceptable disalt thereof, and a pharmaceutically acceptable carrier, to treat a condition, and a pharmaceutically acceptable carrier.

BRIEF DESCRIPTION OF THE DRAWINGS

Many aspects of the disclosed compositions and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIGS. 22A-C illustrates a Table describing the dose response study to evaluate motor coordination in rats.

FIGS. 23A-C illustrates a Table describing the dose response study to evaluate motor coordination in rats.

FIG. 25 is a Table showing the tabulation of IC50 values for the action of the drugs at NMDA receptor subtypes.

DISCUSSION

Figure 1:
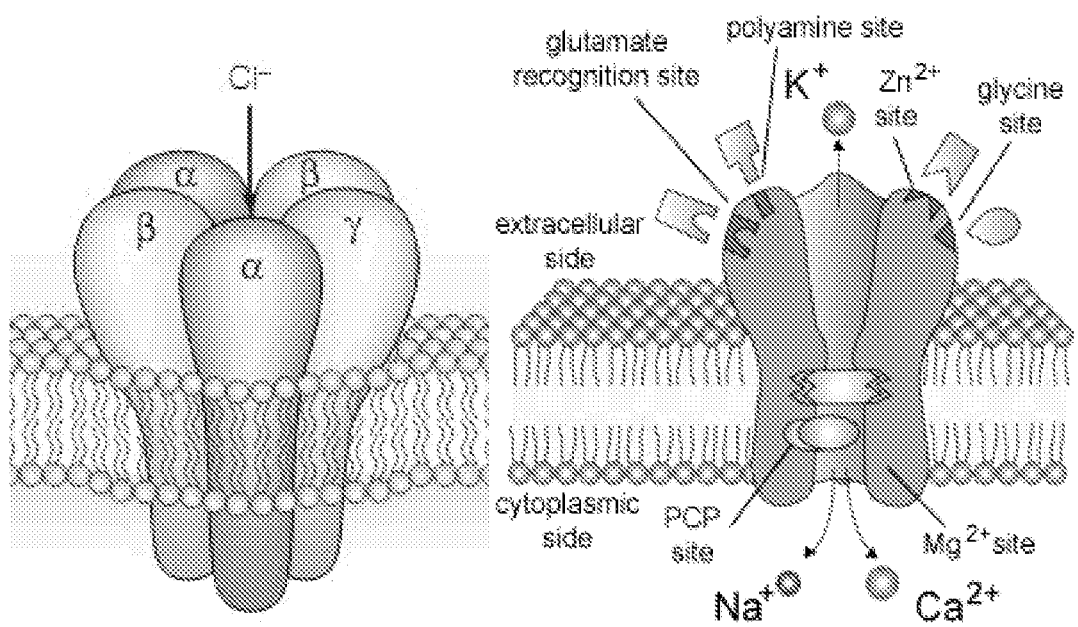
FIG. 1 illustrates a general representation of $GABA_a$ (Left) and NMDA (Right) receptors.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS Pharm Sci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure into a host. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition, a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of a tumor or a disease in a host (e.g., a mammal, typically a human or non-human animal of veterinary interest), and includes: (a) reducing the risk of occurrence of the disease in a subject determined to be predisposed to the condition or disease but not yet diagnosed with it (b) impeding the development of the condition or disease, and/or (c) relieving the condition disease, e.g., causing regression of the condition or disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition, a disease, or a symptom thereof and/or may be therapeutic in terms of a partial or complete cure for a condition, a disease, and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The term "substituted" refers to any one or more hydrogens on the designated atom that can be replaced with a selection from the indicated group, provided that the designated atom's normal valence is not exceeded, and that the substitution results in a stable compound that has similar characteristics as the parent compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

Discussion

Embodiments of the present disclosure provide compositions including ketamine analogues, salts, and disalts, pharmaceutical compositions including ketamine analogues, salts, or disalts, methods of treatment of a condition or disease, methods of treatment using compositions or pharmaceutical compositions, and the like.

Embodiments of the ketamine analogues were synthesized with an aim of inhibiting NMDA receptors and stimulating GABAa receptors in an effort to enhance the clinical therapeutic properties of ketaminer while minimized undesirable side effects.

An embodiment of the present disclosure can be used as an anesthetic, analgesic, and/or antidepressant, when given to a subject in an appropriate therapeutically effective amount. In addition, an embodiment of the present disclosure can be used in the treatment of phantom pain, epilepsy, and/or depression. Furthermore, an embodiment of the present disclosure may have a reduced hallucinogenic effect on subjects relative to ketamine. Additional details are described in the Examples.

An embodiment of the present disclosure includes a composition and a pharmaceutical composition including a ketamine analogue, a salt thereof, or a disalt thereof. In an embodiment, the pharmaceutical composition includes a therapeutically effective amount of a ketamine analogue, or a pharmaceutically acceptable salt of the ketamine analogue (e.g., a pharmaceutically acceptable salt thereof, or pharmaceutically acceptable disalt thereof), and a pharmaceutically acceptable carrier, to treat a condition (e.g., neuropathic pain (phantom pain), epilepsy, and/or depression) and/or can be used as an anesthetic, analgesic, and/or antidepressant.

In an embodiment, the ketamine analogue can include compounds represented by structures I to IX in FIG. 16 below, in which each structure can be substituted or unsubstituted so long as the substitution results in a compound that has similar or superior characteristics as the parent compound. In an embodiment, one or more of H can be independently substituted on any of the rings in the structures I to IX with a halogen, an aliphatic group (e.g., an alkyl group (e.g., C1 to C5 hydrocarbons such as methyl, ethyl, and the like)), an aryl group, a fused aryl group, a cyclic group (e.g., a cyclic alkyl group), and a heteroaryl group, where any one of these groups can be substituted or unsubstituted, where such substitution does not substantially modify the function and is consistent with the ketamine analogues as described herein.

In an embodiment, the ketamine analogue can include a salt of the ketamine analogue or a disalt of the ketamine analogue. For example, the ketamine analogue can include the salt (e.g., chloride salt) and the disalt (e.g., chloride disalt) of the compounds represented by structure VII (protenation of the oxime and/or primary imine of the oxime). See Example 1 for additional details.

In an embodiment, a ketamine analogue, a salt, or a disalt, can be used to treat or prophylactically treat a condition or disease such as phantom pain, epilepsy, and/or depression. In an embodiment, a ketamine analogue, a salt, or a disalt, can be used as an anesthetic, analgesic, and/or antidepressant when given to a subject in an appropriate therapeutically effective amount. In particular, a composition or a pharmaceutical composition that includes a therapeutically effective amount of a ketamine analogue, or a pharmaceutically acceptable salt (e.g., a salt, or a disalt) of the ketamine analogue, and a pharmaceutically acceptable carrier is delivered to a subject of need of treatment or prophylactic treatment.

In an embodiment, a ketamine analogue, a salt, or a disalt, can be used to increase GABAA receptor activity while retaining the blocking action on the NMDA receptors, relative to phencyclidine. In particular, a composition or a pharmaceutical composition that includes a therapeutically effective amount of a ketamine analogue, or a pharmaceutically acceptable salt (e.g., a salt, or a disalt) of the ketamine analogue, and a pharmaceutically acceptable carrier is delivered to a subject of need of treatment. Administration of the composition or pharmaceutical composition can increase GABAA receptor activity, while retaining the blocking action on the NMDA receptors, relative to phencyclidine.

It should be noted that the therapeutically effective amount to result in uptake of the ketamine analogue into the host will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Pharmaceutical Formulations and Routes of Administration

Embodiments of the present disclosure include a ketamine analogue, a salt, or a disalt, as identified herein and formulated with one or more pharmaceutically acceptable excipients, diluents, carriers and/or adjuvants. In addition, embodiments of the present disclosure include a ketamine analogue, a salt, or a disalt, formulated with one or more pharmaceutically acceptable auxiliary substances. In particular, a ketamine analogue can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the ketamine analogue, the salt, or the disalt, can be administered to the host using any means capable of resulting in the desired effect. Thus, the ketamine analogue, the salt, or the disalt, can be incorporated into a variety of formulations for therapeutic administration. For example, the ketamine analogue, the salt, or the disalt, can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the ketamine analogue may be administered in the form of its pharmaceutically acceptable salts (e.g., a salt or disalt), or a subject active composition may be used alone or in appropriate association, as well as in combination, with other pharmaceutically active compounds. The following methods and excipients are merely exemplary and are in no way limiting.

For oral preparations, the ketamine analogue, the salt, or the disalt, can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the ketamine analogue, the salt, or the disalt, can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the ketamine analogue, the salt, or the disalt, can be utilized in aerosol formulation to be administered via inhalation. Embodiments of the ketamine analogue can be formulated into pressurized acceptable propellants such as dichlorodifluoromethane, propane, nitrogen and the like.

Furthermore, embodiments of the ketamine analogue, the salt, or the disalt, can be made into suppositories by mixing with a variety of bases such as emulsifying bases or water-soluble bases. Embodiments of the ketamine analogue, the salt, or the disalt, can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the ketamine analogue in a composition as a solution in sterile water, normal saline or another pharmaceutically acceptable carrier.

Embodiments of the ketamine analogue, the salt, or the disalt, can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the ketamine analogue, the salt, or the disalt, can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the the ketamine analogue, the salt, or the disalt, can be accomplished using any of a variety of refillable, pump systems. Pumps provide consistent, controlled release over time. In some embodiments, the ketamine analogue, the salt, or the disalt, can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the ketamine analogue, the salt, or the disalt) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the ketamine analogue, the salt, or the disalt, are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the ketamine analogue, the salt, or the disalt, adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the ketamine analogue, the salt, or the disalt, may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the ketamine analogue described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the ketamine analogue, the salt, or the disalt, can be administered to a host in one or more doses. Those of skill will readily appreciate that dose levels can vary as a function of the specific the ketamine analogue, the salt, or the disalt, administered, the severity of the symptoms and the susceptibility of the subject to side effects. Preferred dosages for a given compound are readily determinable by those of skill in the art by a variety of means.

In an embodiment, multiple doses of the ketamine analogue, the salt, or the disalt, are administered. The frequency of administration of the ketamine analogue, the salt, or the disalt, can vary depending on any of a variety of factors, e.g., severity of the symptoms, and the like. For example, in an embodiment, the ketamine analogue, the salt, or the disalt, can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the ketamine analogue, the salt, or the disalt, is administered continuously.

The duration of administration of the ketamine analogue, the salt, or the disalt, e.g., the period of time over which the ketamine analogue is administered, can vary, depending on any of a variety of factors, e.g., patient response, etc. For example, the ketamine analogue, the salt, or the disalt, in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the ketamine analogue, the salt, or the disalt,) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the ketamine analogue, the salt, or the disalt,) can be administered in a single dose or in multiple doses.

Embodiments of the ketamine analogue, the salt, or the disalt, can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the ketamine analogue. Where systemic delivery is desired, administration typically involves invasive or systemically absorbed topical or mucosal administration of pharmaceutical preparations.

In an embodiment, the ketamine analogue, the salt, or the disalt, can also be delivered to the subject by enteral administration. Enteral routes of administration include, but are not limited to, oral and rectal (e.g., using a suppository) delivery.

Methods of administration of the ketamine analogue, the salt, or the disalt, through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Introduction

Ligand gated ion channels are membrane-embedded proteins at synaptic clefts which control intercommunication among neurons. Each receptor has a function of allowing the flow of ions like Cl⁻, Na⁺, K⁺ resulting in excitation or inhibition. When a neurotransmitter like γ-aminobutyric acid (GABA) binds to its respective receptor-channel (GABA receptors), chloride ions flow through the receptor[1] channel reducing the likelihood of initiating action potentials. $GABA_a$ receptors[2] are the most ubiquitously expressed ligand gated Cl⁻ ion channels in the mammalian central nervous system.[3] These receptors are assembled from a diverse family of 19 homologous subunits[4] ($\alpha_{(1-6)}$, $\beta_{(1-3)}$, $\gamma_{(1-3)}$, $\delta$, $\pi$, $\theta$, $\epsilon$ and $\rho_{(1-3)}$), which are differentially expressed throughout the brain.[5] The $GABA_a$ receptor is a pentameric complex composed of closely related subunits in 2:2:1 stoichiometry in which α, β and γ subunits expressed as most abundant subunits (FIG. 1).[6] From previous studies with transgenic mice and with subtype selective subunits, it has been established that while α1-containing receptors are responsible for mediating sedative and muscle relaxant properties, α3 and/or α2-containing receptors are responsible for anxiety.

Subtypes $\alpha_6\beta_{2/3}\delta$ in the $GABA_a$ receptor are expressed at high levels within mature cerebellar granule neurons.[7] Cerebellar granule cells are the most abundant neurons in the CNS. They play a pivotal role in cerebellar motor control[8] and learning activities. γ-Aminobutyric acid (GABA) is a major inhibitory neurotransmitter and an agonist of GABA receptors. When GABA binds GABAa receptors, the pore opens to allow ion influx[9] which leads to inhibitory neurotransmission. $GABA_a$ receptors also contain a site of action for a number of allosteric modulators like neurosteriods, ethanol, benzodiazepines,[5,10] barbiturates,[11] picrotoxin,[12] zinc cations,[13] loreclazole[14] and anesthetics including thiopental,[15] propofol[16] and etomidate.[17]

In contrast N-methyl-D-aspartate (NMDA) receptors[18] are glycine and glutamate gated receptors. When a neurotransmitter binds to NMDA receptors, the pore opens to allow influx of cations[19] like Ca⁺ ions which are implicated in synaptic plasticity and learning.[20] The influx of Ca⁺ ions into neuronal cell results membrane depolarization causing the propagation of excitory signals and also triggering intracellular signaling pathways.[21] Overactivation of these receptors has been implicated in conditions such as ischemic stroke and traumatic brain injury,[22] where the glutamate levels are elevated. In the central nervous system (CNS), subunits like NR1, NR2 and NR3 form the heterotetrameric NMDA receptor complex.[23] Two NR1 and two NR2A or NR2B subunits assemble in a hetereotetrameric complex to form the most common NMDA receptors in adult CNS (FIG. 1). In general, NMDA receptors contribute to differing biophysical and pharmacological properties.[23]

Figure 2:
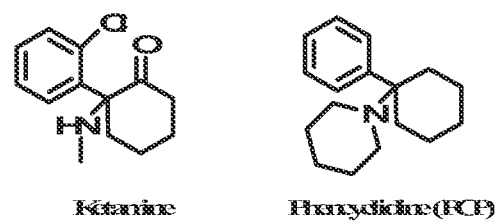
FIG. 2 illustrates structures of Ketamine and Phencyclidine (PCP).

Ketamine and phencyclidine (PCP) (FIG. 2), known as dissociative anesthetics, produce profound analgesia at low doses, compared to cardiovascular stimulation and a cataleptic state at higher doses.[24] Both ketamine and PCP, primarily acting at NMDA receptors as uncompetitive antagonists[25] via reducing excitory input. PCP shows markedly higher affinity[26] for this target compared to ketamine. However, ketamine possesses a higher overall CNS depressant activity and produces a better quality of anesthesia than PCP.[27] Neurotransmitter systems like dopamine D2 receptors,[28] 5-HT2 receptors,[29] mu and kappa opioid receptors,[30] sigma receptors and muscarinic cholinergic receptors,[31] voltage gated K⁺, Na⁺ and Ca²⁺ channels[32] are also shown to be affected by ketamine and PCP at significantly higher concentrations.

Studies have yet to determine the mechanism by which ketamine produces a higher overall CNS depression than PCP while at anesthetic doses.[33] Dose-dependent side effects like vivid dreams, illusions, disruptions of cognitive function, and mood changes have been reported with ketamine administration, which are also observed in schizophrenia.[34] The psychotomimetic effects of the ketamine have been shown or proposed to mediated by its inhibitory effect on GABAergic interneurons leading to increase in the glutamate release.[35] Administration of subanesthetic doses of ketamine have been shown to have therapeutic efficacy for the treatment resistant major depression.[36] Other side effects associated with ketamine (saccade, nystagmus, hyperlocomotion and prepulse inhibition deficit) make it a useful model system[37] to study schizophrenia and to identify compounds for the inhibition of a ketamine induced hyperlocomotion for the schizophrenic studies in animals. However, previously described ketamine analogues[38] have thus far been unable to broaden ketamine's desired therapeutic clinical effects, or decrease the incidence of side effects.

Only few reports exist toward the efforts to synthesize ketamine analogues. Yang et. al. synthesized amino tetralone analogues of ketamine (Scheme 1) for locomotor activity tests in mice.[38b] In these compounds, a benzene ring was fused with a cyclohexanone ring restricting conformational flexibility. 1-amino-1-methyl-2-tetralone was synthesized starting from 2-amino-2-phenyl-propionic acid via intermediate pthalimidophenyl acetylchloride. 2-amino-2-methyl-1-tetralone was synthesized from benzyl acetone via amino cyanide intermediate (see Scheme 1).

Scheme 1. Synthesis of tetralone analogues of ketamine by Yang et. al.

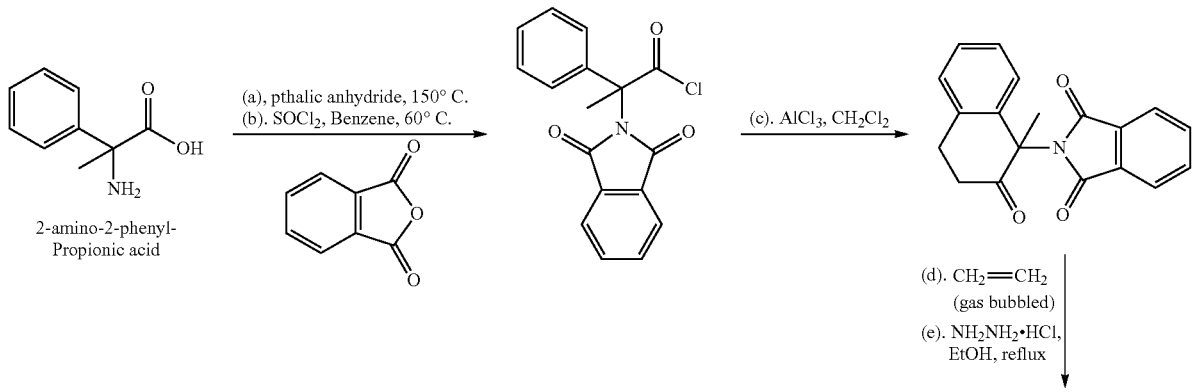

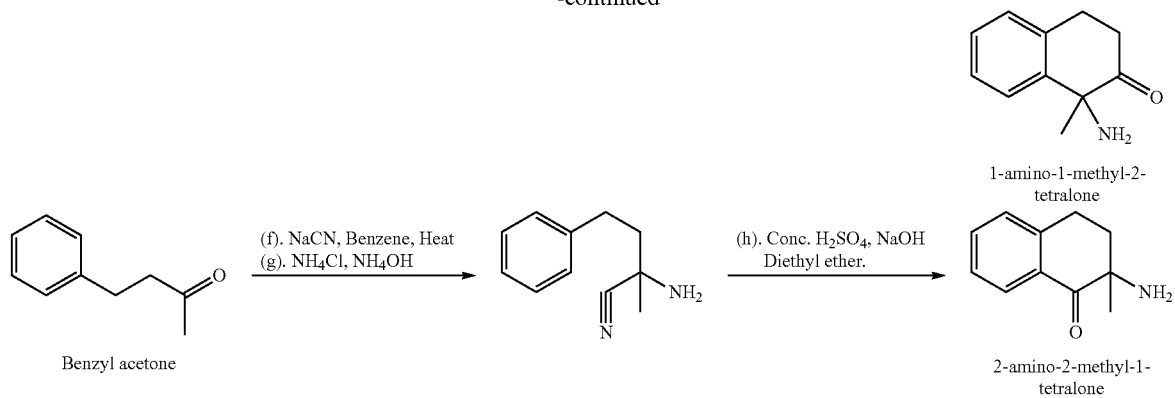

Though none of the tetralones produced hypnosia or profound ataxia, 2-amino-2-methyl-1-tetralone caused an increased locomotor activity while 1-amino-1-methyl-2-tetralone decreased, but was not significant when compared with ketamine.

Recently, Zarantonello et. al. reported novel ketamine analogues. In their strategy, ketamine was modified by introducing amide in cyclohexanone ring and with various tertiary and secondary amines attached in the place of methylamine for evaluation as NMDA receptor antagonists.[39] Ketamine analogues A and B, which have amide group in cyclohexanone ring (Scheme 2) were synthesized from chlorophenyl amine acetic acid. Intermediate amino nitrile was synthesized from chlorophenyl amineacetic acid by alkylation. Upon reductive cyclization of this intermediate in the presence of $CoCl_2$ and $NaBH_4$, the resulting cyclic amide was further methylated with methyl iodide to isolate novel analogues A and B as a mixture which were separated by HPLC purification.

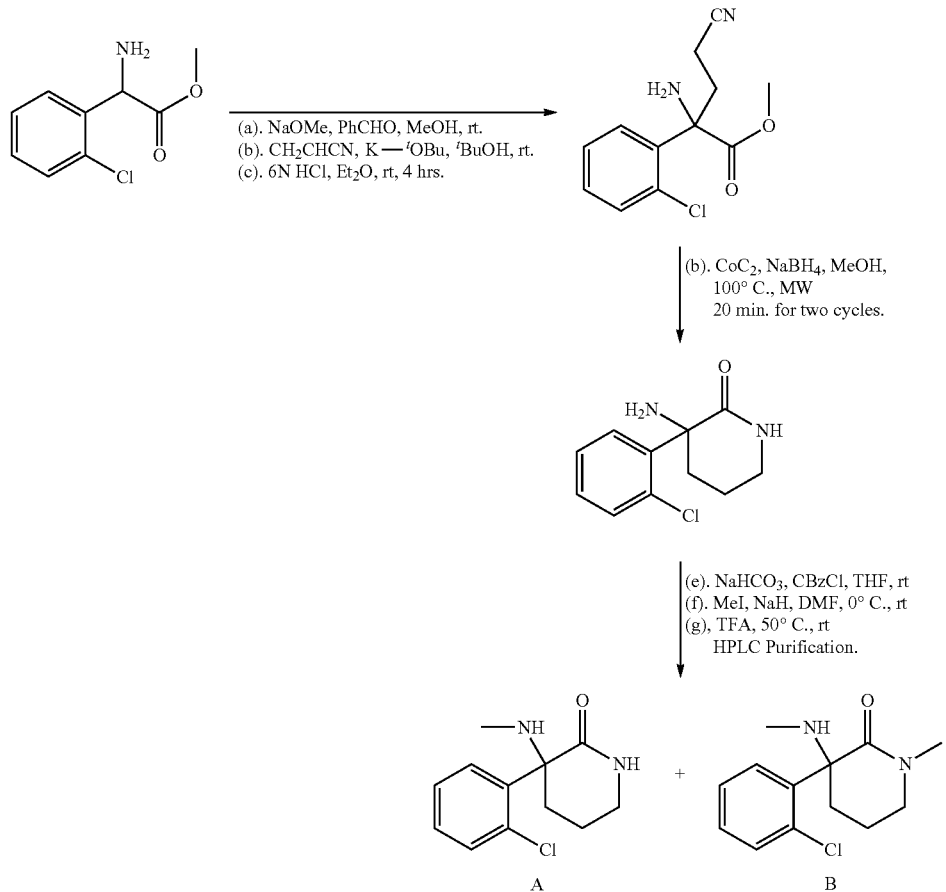

Scheme 2. Synthesis of lactam with methylamine analogues of ketamine by Zarantonello et. al.

In a similar strategy, analogues of phencyclidine (C and D) were synthesized from bromophenyl methylacetate via piperidine nitrile intermediate (see Scheme 3). Nitrile group in this intermediate was then reduced and cyclized in the case of synthesis of six membered ring as in C and cyclized directly by reductive hydrogenation in the case of synthesis of 5 membered ring as in D. Methylated amides (E and F) were synthesized from the amides (C and D) by methylation.

The evaluation of A and B against NMDA receptors with NR2-A and NR2-B subunits showed that an amide functionality in the cyclohexanone ring was not tolerated. The same loss of functional activity was observed even in the case of C-F in comparison to ketamine.

Scheme 3. Synthesis of lactam with piperidine analogues of ketamine by Zarantonello et. al.

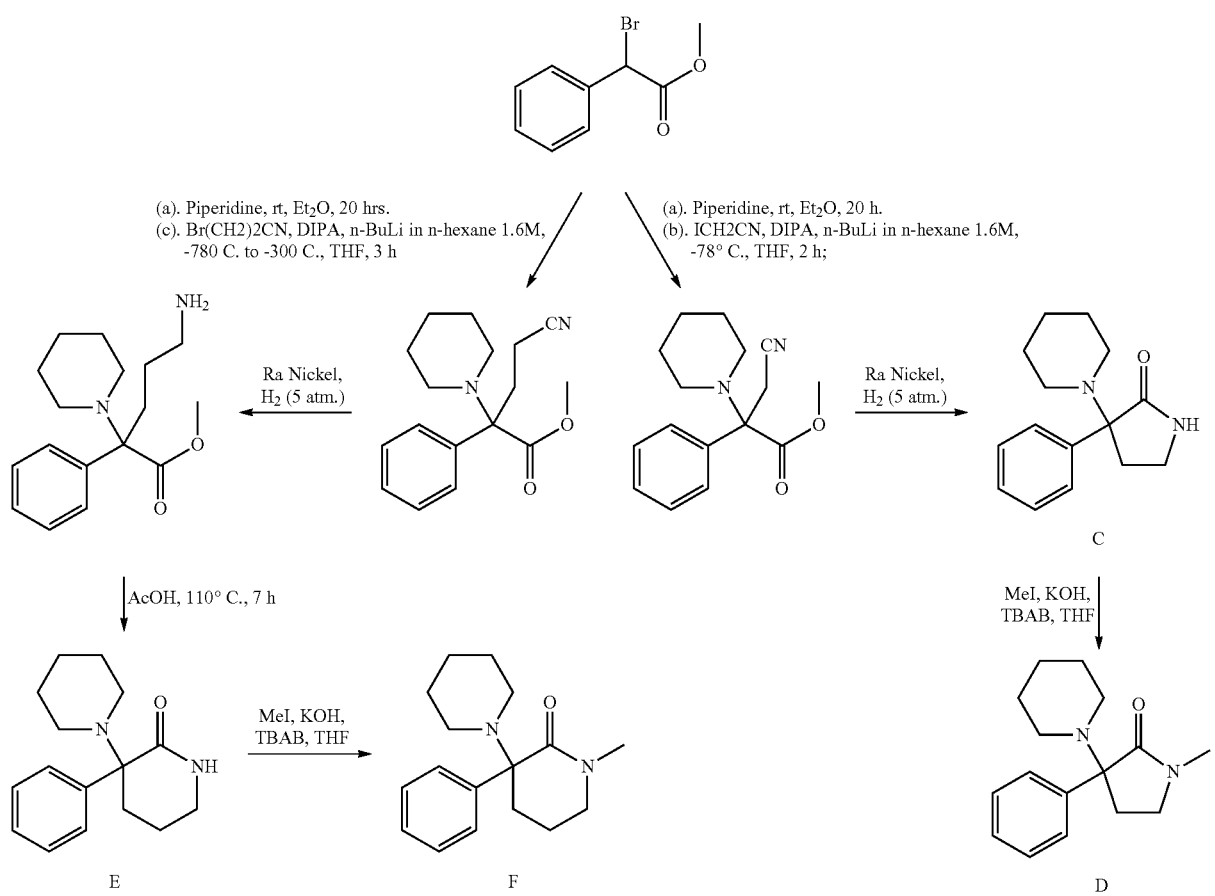

From these structure-activity relationship studies, any appreciable activity was observed only in the analogue (G) in which cyclohexyl ring was preserved and phenyl group has a methoxy substituent (Scheme 4).

Scheme 4. Synthesis of ketamine analogue with phenyl group substitution.

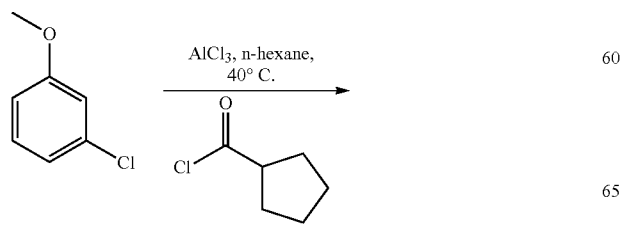

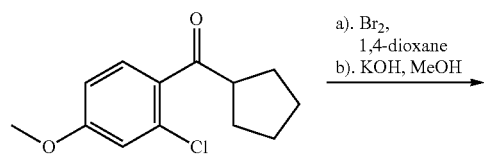

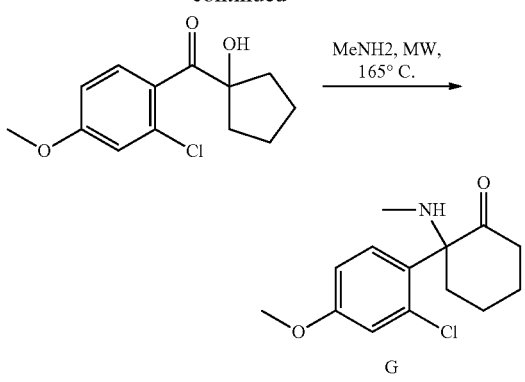

Synthesis of Novel Ketamine Analogues

Figure 3:
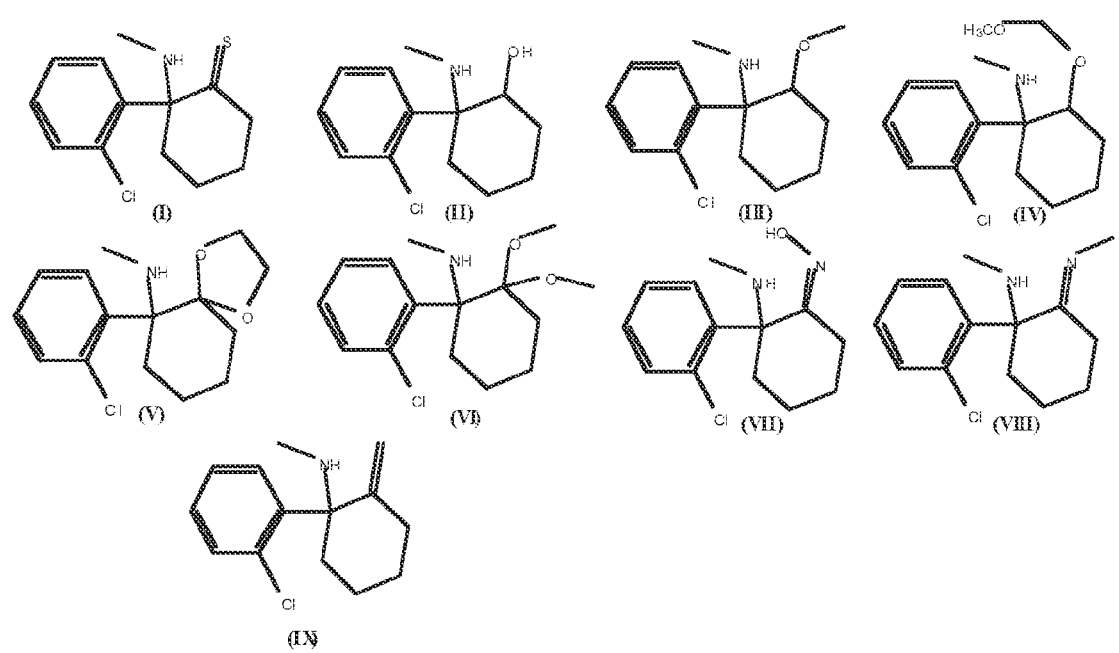
FIG. 3 illustrates embodiments of the present disclosure.

Previously reported ketamine analogues with modification of cyclohexyl ring to amide[39] (Scheme 2 and 3) or fused cyclohexane with benzene[38b] (Scheme 1) resulted in a loss of functional activity. The functional activity was sustained only when cyclohexyl ring is preserved (Scheme 4) in ketamine or phencyclidine. When the phenyl group was introduced with various substitutions, the activity was modestly retained in comparison with ketamine. In the present invention, we sought to synthesize novel analogues of ketamine with cyclohexyl ring intact, by transforming the carbonyl group in cyclohexane to a few other analogues with imine substitutions as depicted in Scheme 5, Table 1, and FIG. 3.

Scheme 5. Synthesis of ketamine analogues of the present invention. See Table 1 for appropriate reagents and conditions.

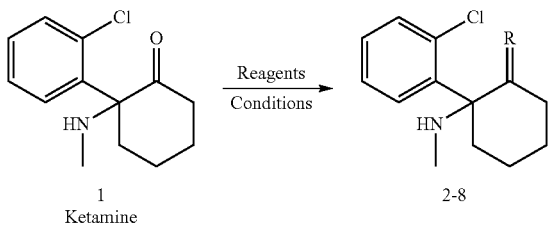

TABLE 1

Reagents and Conditions to synthesize ketamine analogues.

| Entry | Reagents | Solvent | Conditions | Yield | Product |
|---|---|---|---|---|---|
| 1 | $NH_2OH \cdot HCl$, $CH_3COONa \cdot H_2O$ | MeOH:$H_2O$ (7:3) | reflux | 70% | 2 — Oxime |
| 2 | $NH_2OMe \cdot HCl$, $CH_3COONa \cdot H_2O$ | MeOH:$H_2O$ (7:3) | reflux | 78% | 3 — Methoxime |
| 3 | $NH_2OPh \cdot HCl$, $CH_3COONa \cdot H_2O$ | MeOH:$H_2O$ (7:3) | reflux | 90% | 4 — Benzoxime |
| 4 | $NH_2CONHNH_2 \cdot HCl$, $CH_3COONa \cdot H_2O$ | MeOH:$H_2O$ (7:3) | reflux | 60% | 5 — Semicarbazone |
| 5 | $NaBH_4$ | MeOH | r. temp. | 80% | 6 — Hydroxy |
| 6 | $(Ph_3P)_3PCH_3Br$, n-BuLi, | dry. THF | −78° C. to r. temp. | | No Product |
| 7 | $MeNH_2 \cdot HCl$, $CH_3COONa \cdot H_2O$, | MeOH or $CH_2Cl_2$ or Toluene | reflux | | Product is unstable |

TABLE 1-continued

Reagents and Conditions to synthesize ketamine analogues.

| Entry | Reagents | Solvent | Conditions | Yield | Product |
|---|---|---|---|---|---|
| 8 | $NH_2$—$NH_2$•HCl, Pyridine | MeOH | reflux | | Product is unstable |
| 9 | $NH_2CSNHNH_2$•HCl, $CH_3COONa$•$H_2O$, | MeOH: $H_2O$ (7:3) | reflux | | No Product |

Figure 4:
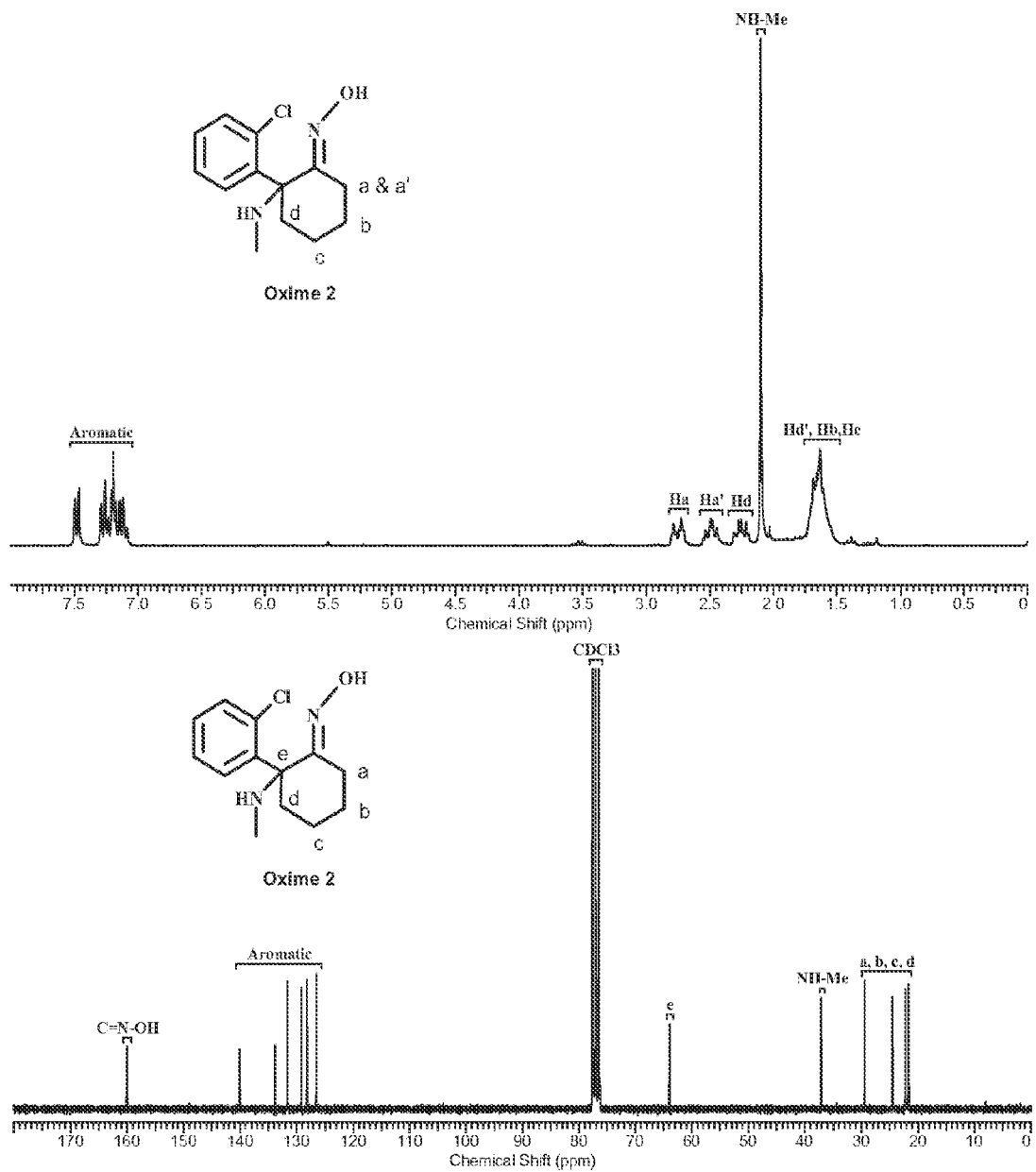
FIG. 4 illustrates NMR Spectra of Oxime 2. TOP. $^1$H NMR. BOTTOM. $^{13}$C NMR.

Ketamine's carbonyl group was converted to the oxime by treating with hydroxylamine in the presence of sodium acetate at reflux to synthesize oxime 2 in 70% yield as a white color solid. The structure of the oxime 2 was confirmed by its NMR spectra (FIG. 4). In a $^1H$ NMR spectrum, methylene hydrogens (Ha and Ha') next to C═N group showed resonance at 2.5 and 2.8 ppm. Carbon in C═N—OH groups showed resonance at 161 ppm in $^{13}C$ NMR. The absence of any signal between 200-220 confirms that ketamine has been transformed to oxime 2. Absence of any isomers of hydroxyl group on C═N could be observed in both $^1H$ and $^{13}C$ NMR spectra (FIG. 4).

Figure 5:
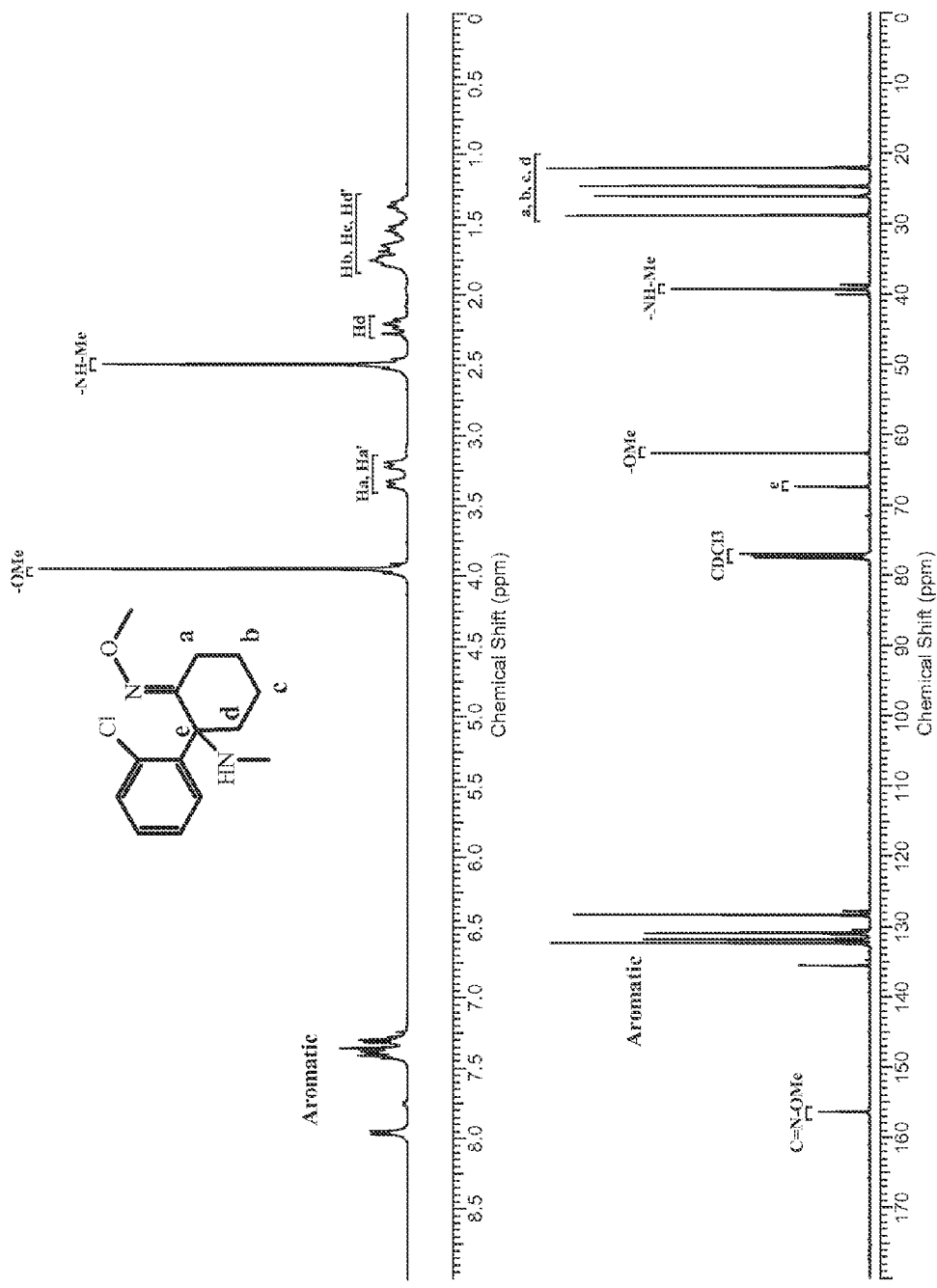
FIG. 5 illustrates NMR Spectra of Methoxime 2. TOP. $^1$H NMR. BOTTOM. $^{13}$C NMR.

In a similar fashion, ketamine 1 was treated with methoxylamine to synthesize methoxime 3. In this reaction, methoxime 3 has obtained in 78% yield as a light yellow color solid. In the structural determination of methoxime 3 by NMR spectra, methylene hydrogens (Ha and Ha') have showed resonance at 3.3 ppm and methoxy hydrogens showed resonance at 3.9 ppm (FIG. 5). In both $^1H$ and $^{13}C$ NMR spectra, isomers of methoxime 3 were also not present (FIG. 5).

Figure 6:
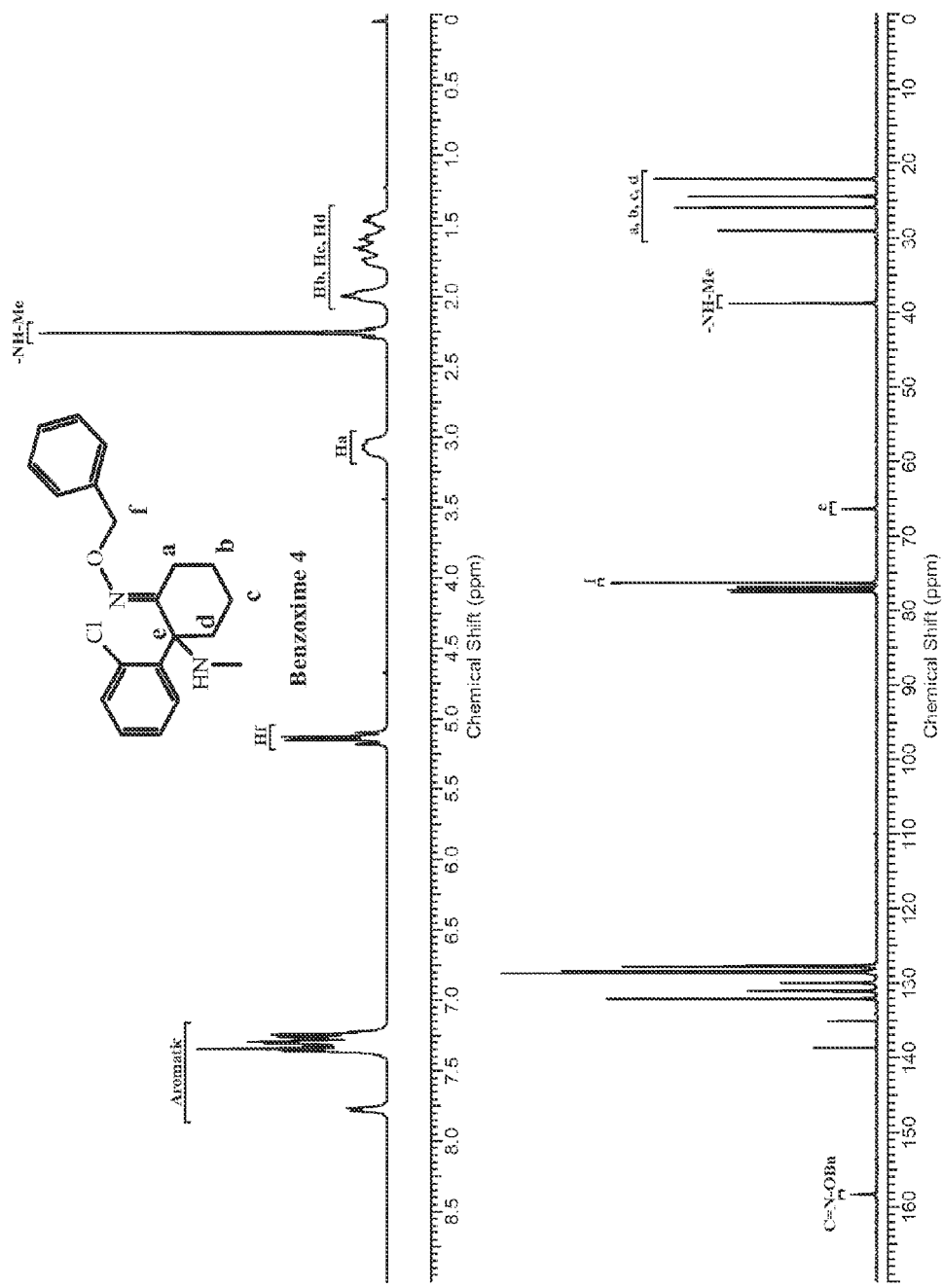
FIG. 6 illustrates NMR Spectra of Benzoxime 4. TOP. $^1$H NMR. BOTTOM. $^{13}$C NMR.

When the ketamine 1 was treated with benzoxylamine in the presence of sodium acetate, benzoxime 4 was isolated as white color solid. Although benzoxylamine group is bulky, the reaction proceeded smoothly yielding the product in 90% yield. Presence of resonance for benzyl methylene hydrogens (Hf) at 5.4 ppm in $^1H$ NMR spectrum and C═N carbon at 158 ppm in $^{13}C$ NMR spectrum confirmed the product. It could be worthy to assume that bulkier benzoxyl group allows the formation of only one isomer which could be observed in $^1H$ and $^{13}C$ NMR spectra (FIG. 6).

Semicarbazone 5 was also synthesized by treating the ketamine 1 with semicarbazide as light yellow color solid. In a wittig reaction with $(PPh_3)_3CH_2PBr$ reagent, the ketamine carbonyl was attempted to convert into a terminal alkene by treating wittig reagent and n-BuLi at low temperature (−78° C.). But the product could not be observed as only the reactant ketamine 1 was recovered. This reaction was repeated with varying equivalent ratios of reagents and temperatures. But in all cases, only ketamine 1 was recovered. So to test the reagent purity, wittig reagent and n-BuLi was treated with benzophenone. In this case, the reaction mixture with 1 hr stirring at room temperature, after addition of benzophenone to wittig reagent and n-BuLi, showed the product on TLC (1:4 EtOAc:Hexanes) which was confirmed in both $^1H$ NMR and $^{13}C$ NMR spectra.

Even in the reactions of ketamine 1 with $HOCH_2CH_2NH_2$. HCl and $NH_2CSNHNH_2$. HCl (Thiosemicarbazide), the product was not observed. In all these reactions, only the reactant ketamine 1 was observed on TLC and NMR spectra. From these reactions, one can assume that ketamine carbonyl group is sterically crowded to be reached by bulky reagent. Methyl amine was also treated with the ketamine 1 to convert into N-methylimine. But the product was not stable even under dry conditions. So the ketamine was recovered as the end product.

Figure 7:
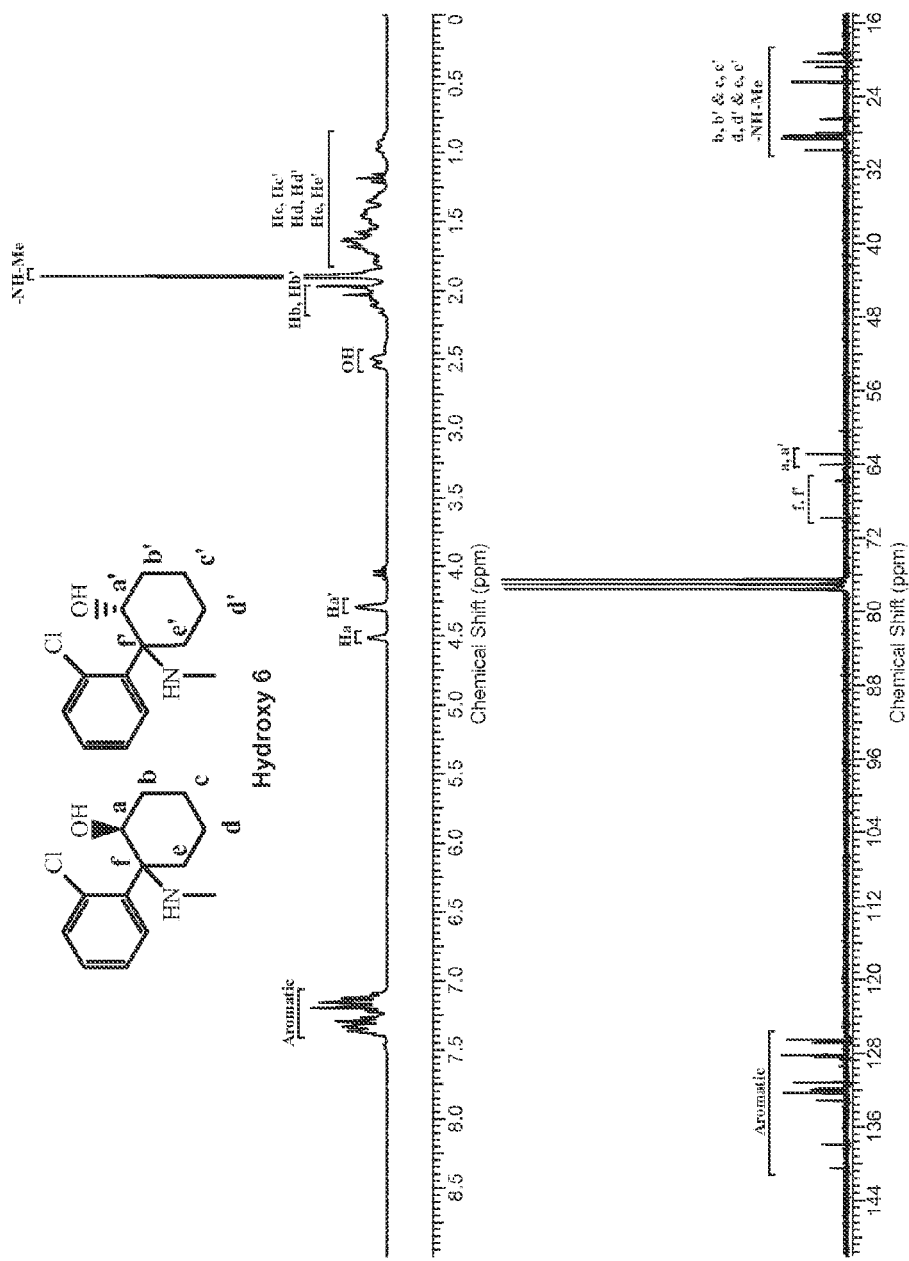
FIG. 7 illustrates NMR Spectra of Hydroxy 6 (Diastereomer ratio 1:0.5). TOP. $^1$H NMR. BOTTOM. $^{13}$C NMR.

The hydroxy analogue 6 was synthesized by treating ketamine 1 with sodium borohydride. This reaction yielded both diastereomers. The presence of the diastereomers was observed on both $^1H$ and $^{13}C$ NMR spectra (FIG. 7). The CH—OH hydrogen (Ha and Ha' in FIG. 7) for both diastereomers showed resonances at 4.5 and 4.25 ppm in the $^1H$ NMR spectrum and the respective CH—OH carbon at 64 and 63 ppm in the $^{13}C$ NMR spectrum. The ratio of diastereomers has been calculated as 7:4 from $^1H$ NMR spectrum. All of the ketamine analogues synthesized was used for the $GABA_A$ and NMDA receptors assay to evaluate their agonist activity at $GABA_A$ receptors and antagonist activity at NMDA receptors. Hydroxy 6 analogue, which received as diastereomeric mixture was used for receptor assay as such without separation.

Experimental Section

General $^1H$-NMR and $^{13}C$-NMR spectra were recorded on a Bruker 250 MHz and Varian 400 MHz spectrometer in $CDCl_3$ and DMSO-d6 with TMS as the standard. Chemical shifts are reported in ppm, multiplicities are indicated by s (singlet), d (doublet), t (triplet), q (quartet), p (quintet), h (sextet), m (multiplet) and bs (broad singlet) coupling constants reported in hertz (Hz). All 13C NMR spectra were proton decoupled. Thin-Layer chromatography (TLC) was performed on glass plates coated with 0.25 mm thickness of silica-gel. All solvents were dried and distilled prior to use and organic solvent extracts were dried over Anhydrous. $Na_2SO_4$. Toluene and tetrahydrofuran were distilled from sodium and benzophenone and were stored in a dry box. Chromatographic purifications were performed by flash chromatography using silica gel (63-200μ) from Dynamic Adsorbents Inc. $Pd(dba)_2$ and $P(t-Bu)_3$ were purchased from Aldrich Inc. All reagents and bases were purchased from Aldrich, Fisher Science, VWR and used without further purification. Aryl bromide 5 was prepared using literature procedure. Ketamine was purchased from Aldrich chemical company and used as received.

2-(2-Chloro-phenyl)-2-methylamino-cyclohexanone oxime (2)

To as solution of $NH_2OH$. HCl and $CH_3COONa$. $H_2O$ in MeOH:$H_2O$ (7:3) stirred at room temperature for 15 minutes, was added ketamine and the resulting solution was stirred at reflux for 16 hrs before cooling to room temperature. The reaction mixture was filtered and the filtrate was partitioned between $CH_2Cl_2$ and sat. $NaHCO_3$ solution. The filtrate was extracted with $CH_2Cl_2$ (2×30 mL) and the combined organic layer was washed with brine solution. The organic layer was dried over anhydrous. Na$_2$SO$_4$ and concentrated under reduced pressure. The crude reaction mixture received was purified over silica gel column chromatography by eluting with initially CH$_2$Cl$_2$ and later with (1:9) MeOH:CH$_2$Cl$_2$ to receive oxime 2 as pale yellow solid. $^1$H NMR (250 MHz, CDCl$_3$) δ 7.4-7.5 (m, 1H), 7.0-7.3 (m, 3H), 2.6-2.8 (m, 1H), 2.4-2.5 (q, J=5.8 Hz, 1H), 2.1-2.3 (m, 1H), 2.0-2.1 (m, 3H), 1.5-1.7 (m, 5H). $^{13}$C NMR (63 MHz, CDCl$_3$) δ 160.1, 140.1, 133.8, 131.6, 129.1, 128.1, 126.5, 64.0, 37.1, 29.4, 24.5, 22.2, 21.7.

2-(2-Chloro-phenyl)-2-methylamino-cyclohexanone O-methyl-oxime (3)

To as solution of NH$_2$OMe. HCl and CH$_3$COONa. H$_2$O in MeOH:H$_2$O (7:3) stirred at room temperature for 15 minutes, was added ketamine and the resulting solution was stirred at reflux for 16 hrs before cooling to room temperature. The reaction mixture was filtered and the filtrate was partitioned between CH$_2$Cl$_2$ and sat. NaHCO$_3$ solution. The filtrate was extracted with CH$_2$Cl$_2$ (2×30 mL) and the combined organic layer was washed with brine solution. The organic layer was dried over anhydrous. Na$_2$SO$_4$ and concentrated under reduced pressure. The crude reaction mixture received was purified over silica gel column chromatography by eluting with initially CH$_2$Cl$_2$ and later with (1:9) MeOH:CH$_2$Cl$_2$ to receive methoxime 3 as pale yellow solid. $^1$H NMR (400 MHz, CDCl$_3$) δ 7.9-8.0 (m, 1H), 7.2-7.4 (m, 3H), 3.91-4.0 (m, 3H), 3.3 (td, J=4.10, 13.96 Hz, 1H), 3.2 (td, J=4.49, 13.73 Hz, 1H), 2.4-2.5 (m, 3H), 2.1-2.3 (m, 1H), 1.6-1.8 (m, 3H), 1.4-1.5 (m, 1H), 1.2-1.4 (m, 1H). $^{13}$C NMR (101 MHz, CDCl$_3$) δ 156.3, 135.5, 132.4, 132.2, 131.9, 131.0, 128.3, 67.4, 62.7, 39.4, 28.8, 26.1, 24.7, 22.0.

2-(2-Chloro-phenyl)-2-methylamino-cyclohexanone O-benzyl-oxime (4)

To as solution of NH$_2$OCH$_2$Ph. HCl and CH$_3$COONa. H$_2$O in MeOH:H$_2$O (7:3) stirred at room temperature for 15 minutes, was added ketamine and the resulting solution was stirred at reflux for 16 hrs before cooling to room temperature. The reaction mixture was filtered and the filtrate was partitioned between CH$_2$Cl$_2$ and sat. NaHCO$_3$ solution. The filtrate was extracted with CH$_2$Cl$_2$ (2×30 mL) and the combined organic layer was washed with brine solution. The organic layer was dried over anhydrous. Na$_2$SO$_4$ and concentrated under reduced pressure. The crude reaction mixture received was purified over silica gel column chromatography by eluting with initially CH$_2$Cl$_2$ and later with (1:9) MeOH:CH$_2$Cl$_2$ to receive benzoxime 4 as pale yellow solid. $^1$H NMR (400 MHz, CDCl$_3$) δ 7.7 (d, J=8.06 Hz, 1H), 7.1-7.4 (m, 8H), 5.0-5.2 (q, J=8.2 Hz, 2H), 2.9-3.1 (m, 2H), 2.2-2.3 (m, 3H), 1.9-2.0 (m, 2H), 1.3-1.8 (m, 4H). $^{13}$C NMR (101 MHz, CDCl$_3$) δ 158.3, 138.7, 135.1, 132.1, 131.1, 129.9, 128.7, 128.4, 127.8, 127.6, 66.4, 38.8, 29.1, 26.0, 24.5, 22.1.

2-(2-Chloro-phenyl)-2-methylamino-cyclohexanone O-semicarbazone (5)

To as solution of NH$_2$CONHNH$_2$. HCl and CH$_3$COONa. H$_2$O in MeOH:H$_2$O (7:3) stirred at room temperature for 15 minutes, was added ketamine and the resulting solution was stirred at reflux for 16 hrs before cooling to room temperature. The reaction mixture was filtered and the filtrate was partitioned between CH$_2$Cl$_2$ and sat. NaHCO$_3$ solution. The filtrate was extracted with CH$_2$Cl$_2$ (2×30 mL) and the combined organic layer was washed with brine solution. The organic layer was dried over anhydrous. Na$_2$SO$_4$ and concentrated under reduced pressure. The crude reaction mixture received was purified over silica gel column chromatography by eluting with initially CH$_2$Cl$_2$ and later with (1:9) MeOH:CH$_2$Cl$_2$ to receive semicarbazone 5 as pale yellow solid. $^1$H NMR (400 MHz, DMSO-d$_6$) δ 9.6 (br. s., 1H), 7.7-7.8 (m, 1H), 7.4-7.5 (m, 3H), 4.0-4.1 (m, 2H), 3.0-3.1 (d, J=4.9 Hz, 2H), 2.1 (s, 3H), 1.5-1.8 (m, 3H), 1.2-1.4 (m, 3H). $^{13}$C NMR (101 MHz, DMSO-d$_6$) δ 158.3, 149.1, 134.8, 133.2, 133.0, 132.3, 128.7, 67.8, 36.8, 28.2, 26.7, 25.9, 22.3.

2-(2-Chloro-phenyl)-2-methylamino-cyclohexanol (6)

To a solution of ketamine in MeOH at 0° C. was added NaBH$_4$ portion wise and allowed to stir at room temperature for 12 hrs. The reaction mixture was cooled to 0° C. and quenched with sat. NH$_4$Cl solution by adding dropwise. The resulting reaction mixture was partitioned between CH$_2$Cl$_2$ and sat. NH$_4$Cl solution and extracted with CH$_2$Cl$_2$ (2×30 mL). The organic layer was dried over anhydrous. Na$_2$SO$_4$ and concentrated at reduced pressure. The crude reaction mixture received was purified over silica gel column chromatography by eluting with (2:8) EtOAc:Hexanes to receive hydroxyl analogue 6 as amorphous white solid. $^1$H NMR (250 MHz, CDCl$_3$) δ 7.2-7.4 (m, 4H), 7.0-7.2 (m, 4H), 4.4-4.5 (m, 1H), 4.2-4.3 (m, 1H), 2.4-2.5 (m, 1H), 1.9-2.1 (m, 2H), 1.8-1.9 (m, 3H), 1.2-1.7 (m, 5H), 0.8-1.0 (m, 1H). $^{13}$C NMR (63 MHz, CDCl$_3$) δ 140.5, 137.9, 133.2, 132.3, 132.0, 131.9, 131.2, 128.3, 126.7, 69.8, 64.0, 62.9, 29.9, 28.7, 28.3, 28.0, 26.5, 22.5, 20.8, 20.3, 19.3.

Figure 8:
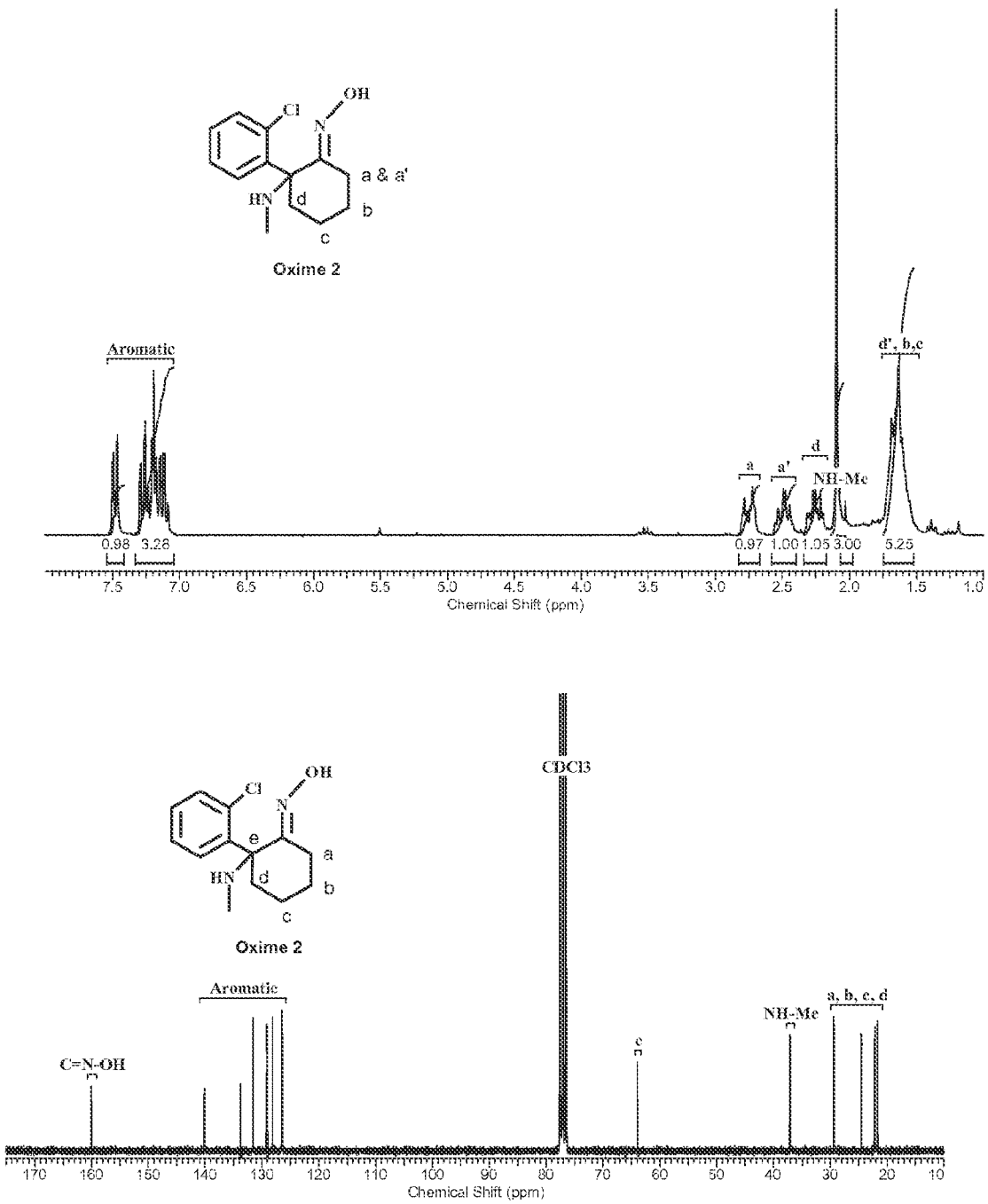
FIG. 8 illustrates $^1$H and $^{13}$C-NMR spectra of 2-(2-Chlorophenyl)-2-methylamino-cyclohexanone oxime (2).
Figure 9:
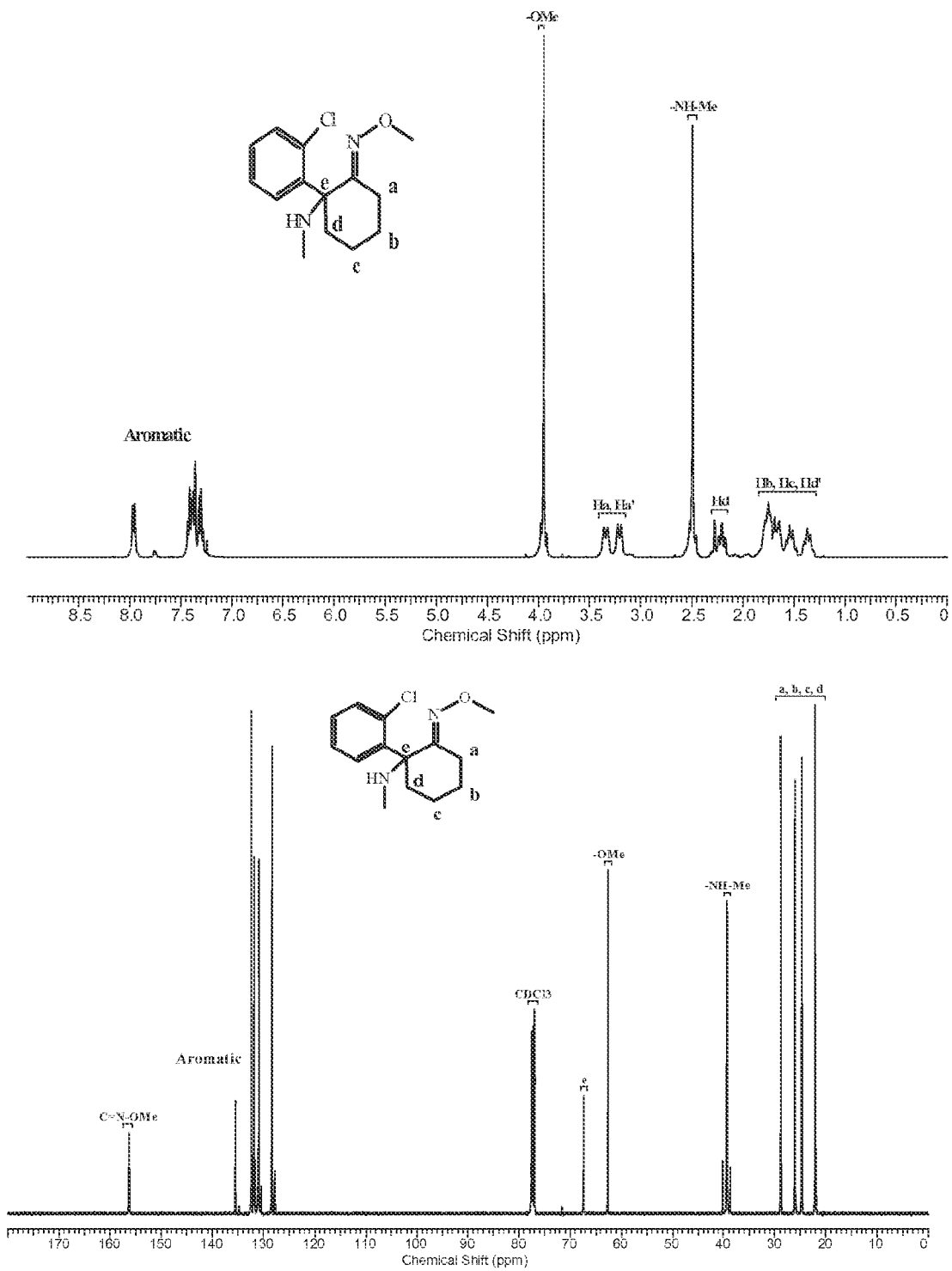
FIG. 9 illustrates $^1$H and $^{13}$C-NMR spectra of 2-(2-Chlorophenyl)-2-methylamino-cyclohexanone O-methyl-oxime (3).
Figure 10:
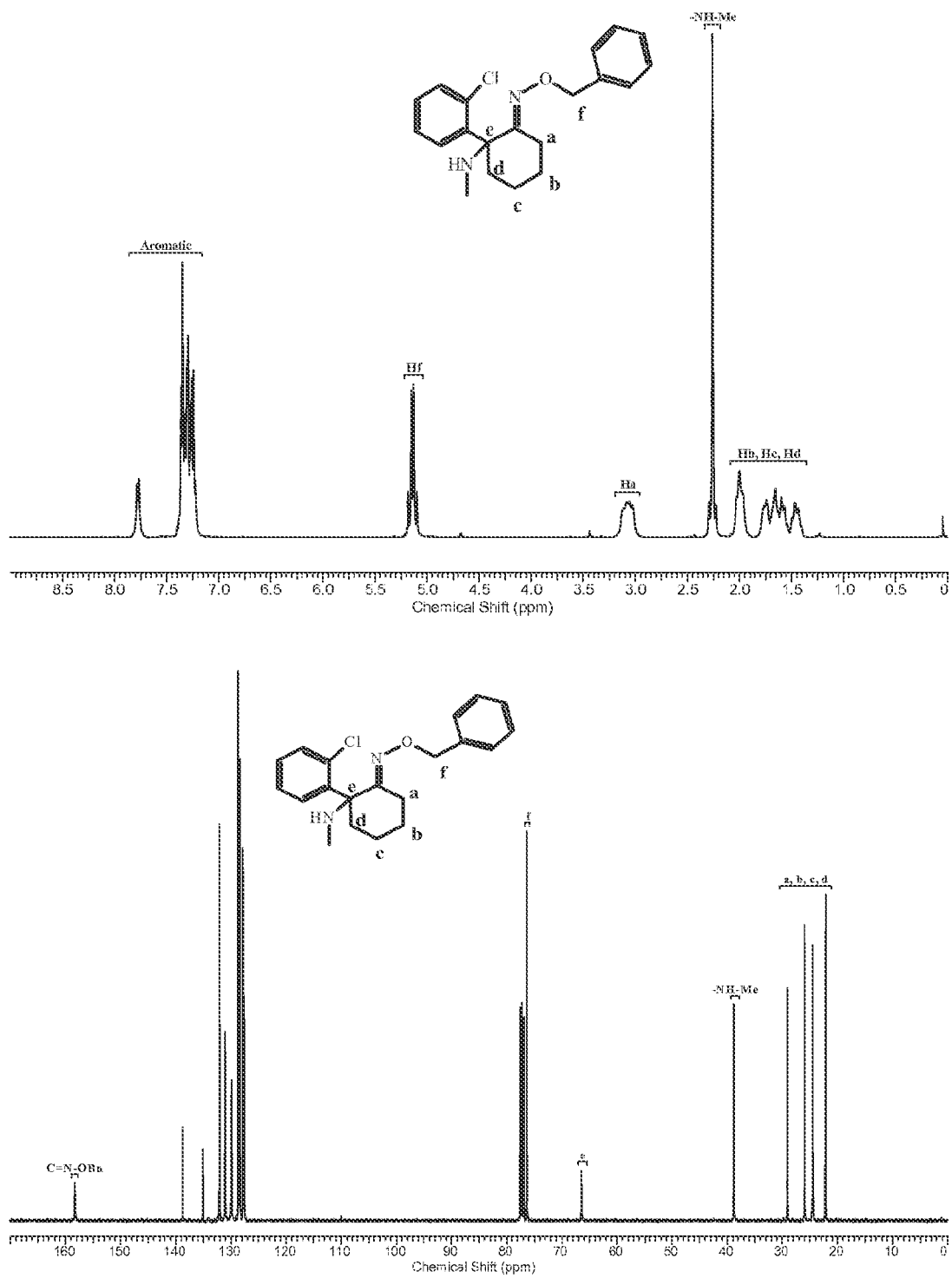
FIG. 10 illustrates $^1$H and $^{13}$C-NMR spectra of 2-(2-Chloro-phenyl)-2-methylamino-cyclohexanone O-benzyl-oxime (4).
Figure 11:
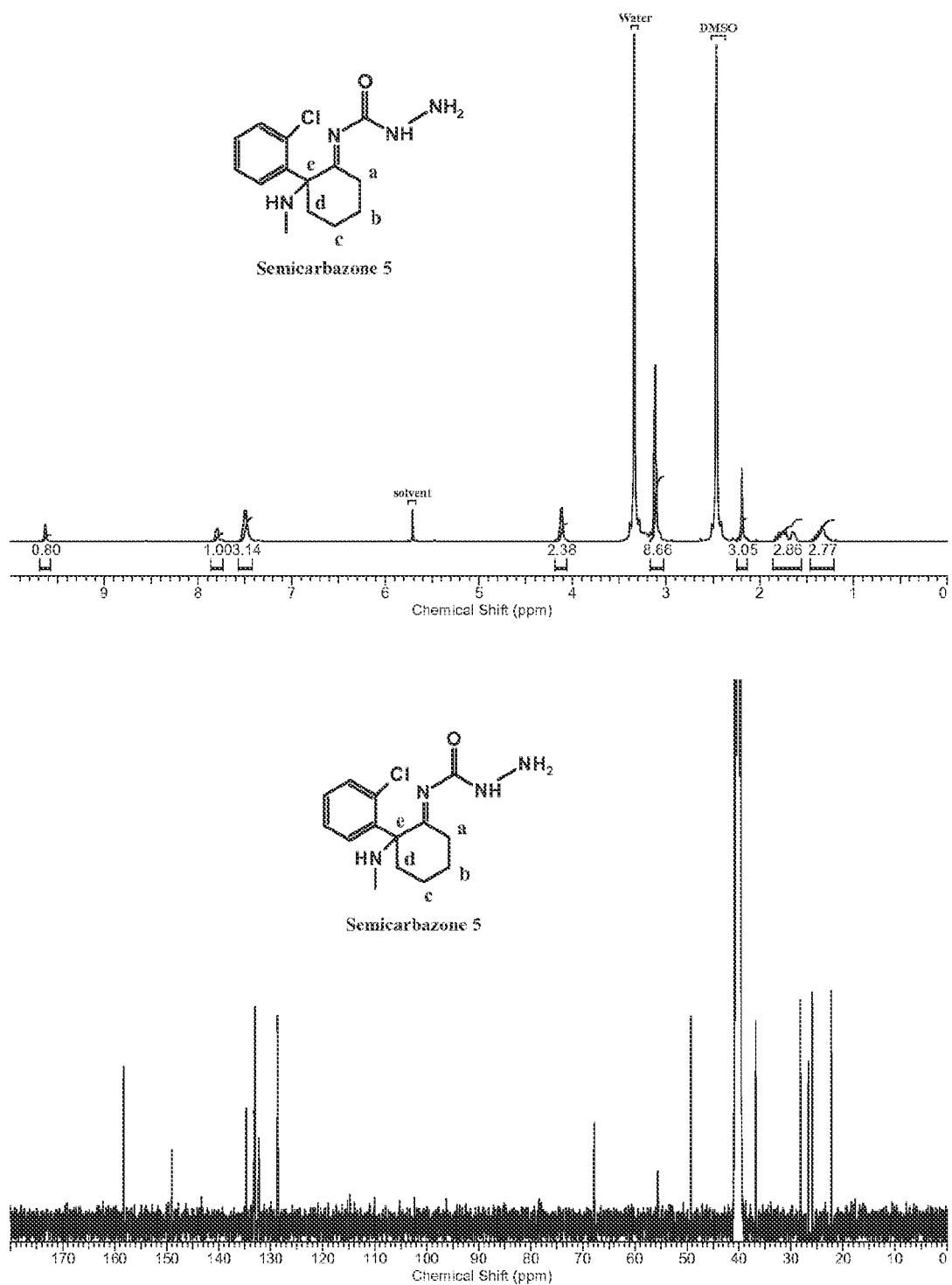
FIG. 11 illustrates $^1$H and $^{13}$C-NMR spectra of 2-(2-Chloro-phenyl)-2-methylamino-cyclohexanone O-semicarbazone (5).
Figure 12:
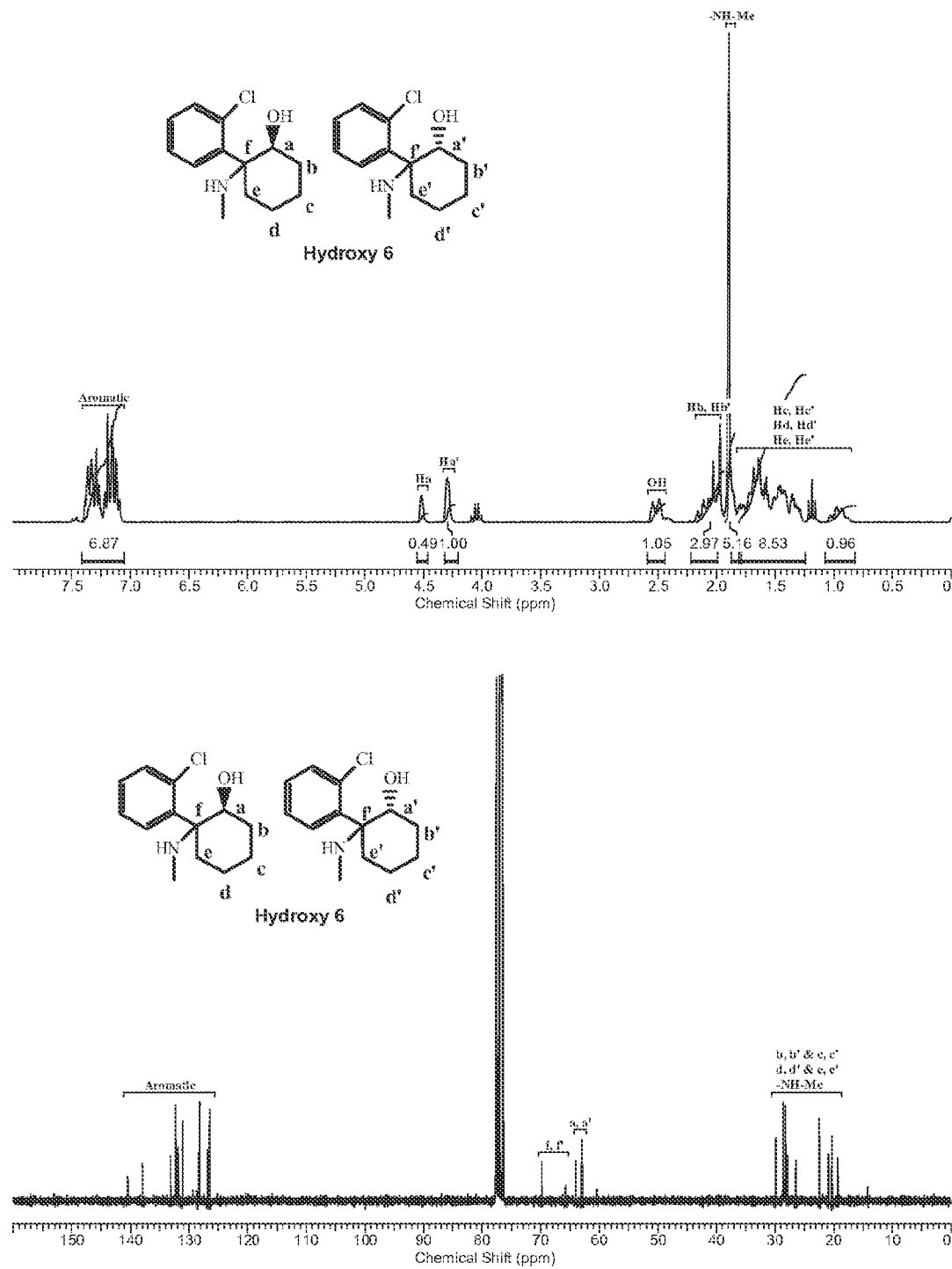
FIG. 12 illustrates $^1$H and $^{13}$C-NMR spectra of 2-(2-Chloro-phenyl)-2-methylamino-cyclohexanol (6).

The following figures provide additional information. FIG. 8 illustrates $^1$H and $^{13}$C-NMR spectra of 2-(2-Chloro-phenyl)-2-methylamino-cyclohexanone oxime (2). FIG. 9 illustrates $^1$H and $^{13}$C-NMR spectra of 2-(2-Chloro-phenyl)-2-methylamino-cyclohexanone O-methyl-oxime (3). FIG. 10 illustrates $^1$H and $^{13}$C-NMR spectra of 2-(2-Chloro-phenyl)-2-methylamino-cyclohexanone O-benzyl-oxime (4). FIG. 11 illustrates $^1$H and $^{13}$C-NMR spectra of 2-(2-Chloro-phenyl)-2-methylamino-cyclohexanone O-semicarbazone (5). FIG. 12 illustrates $^1$H and $^{13}$C-NMR spectra of 2-(2-Chloro-phenyl)-2-methylamino-cyclohexanol (6).

Example 2

Agonist Activities of Ketamine Analogues on GABA a Receptors

The GABA$_a$ subtypes α6β2δ and α1β2γ2 receptors are expressed at high levels exclusively within mature cerebellar granule neurons. In a previous study,[40] ketamine has potentiated the GABA current arising from α6- and δ-containing GABA$_a$ receptors in oocytes, dissociated granule neurons and cerebellar slices isolated from rodents within anesthecally relevant concentration. This earlier study also showed that PCP (Phencyclidine) and Mk-801 (a potent non-competitive inhibitor of NMDA receptor) were less active compared to ketamine in potentiating tonic chloride current arising from GABA$_A$ receptors containing α6- and δ-subtypes. These subtypes were chosen to test the new ketamine analogues of the current invention within an oocyte expression system since their association with cerebellum has a pivotal role in motor control activity.

TABLE 2

Agonist activity of ketamine analogues on GABA$_a$ receptors.

| | α6β2δ[a] | | | | α1β2γ2[a] | |
|---|---|---|---|---|---|---|
| Conc. | Keta-mine | Oxime (Monosalt) | Oxime (Disalt) | Hydroxy | Keta-mine | Oxime (Disalt) |
| 10 | 116.2 | 128.2 | 165.4 | 100 | — | — |
| 20 | 157.1 | 193.746 | 239 | 100 | 0 | 122.678 |
| 50 | 218.3 | 312.04 | 418 | 123.98 | 105 | 153.41 |
| 100 | — | — | — | 135.41 | 119 | 214.5 |

[a]= values depicted are $I_{Average}$ (n. amp). $I_{Average} = (I_{GABA + Drug}/I_{GABA})$ 100.

Figure 13:
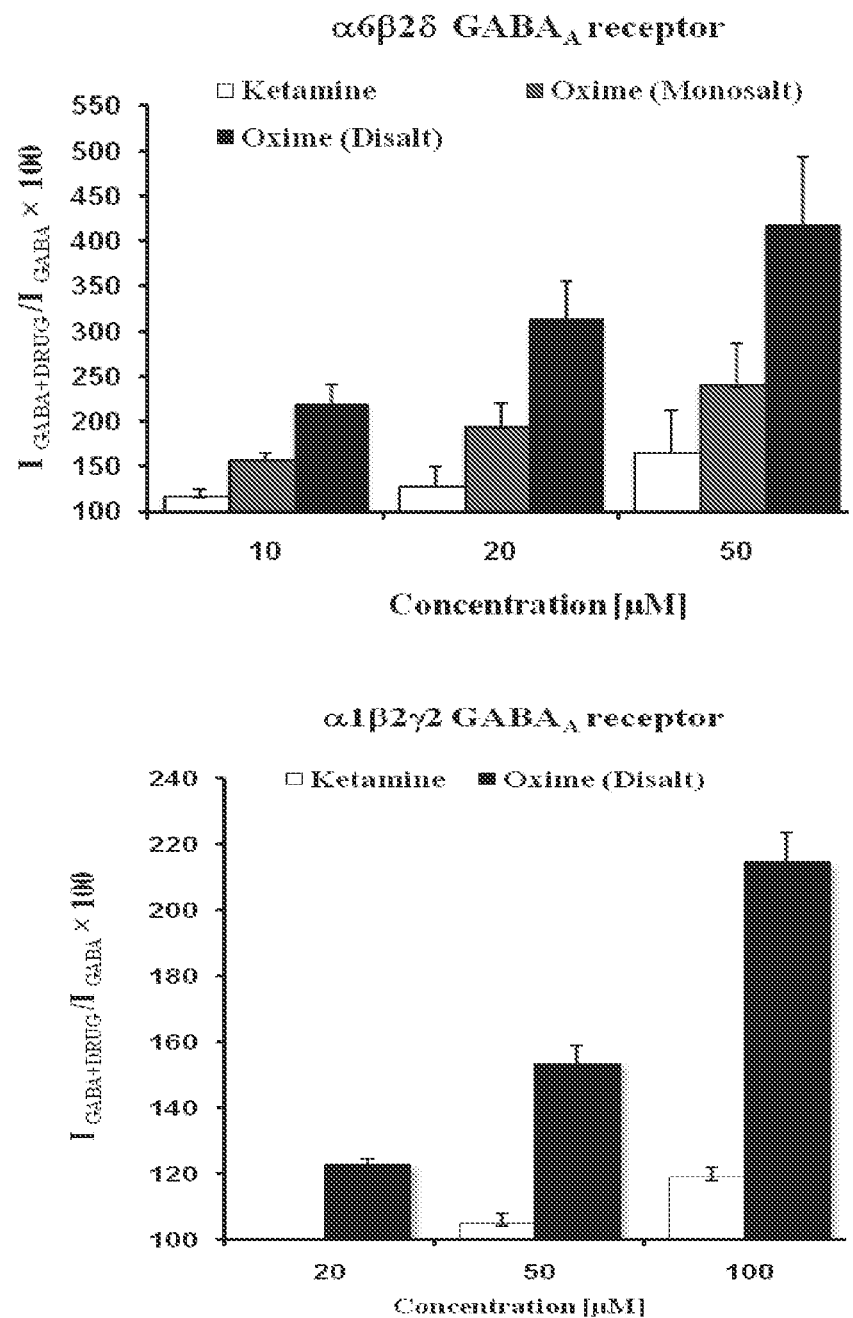
FIG. 13 illustrates agonist activities of ketamine 1 and oxime 2 on $GABA_a$ receptors. TOP. α6β2δ receptors. BOTTOM. α1β2γ2 receptors.
Figure 14:
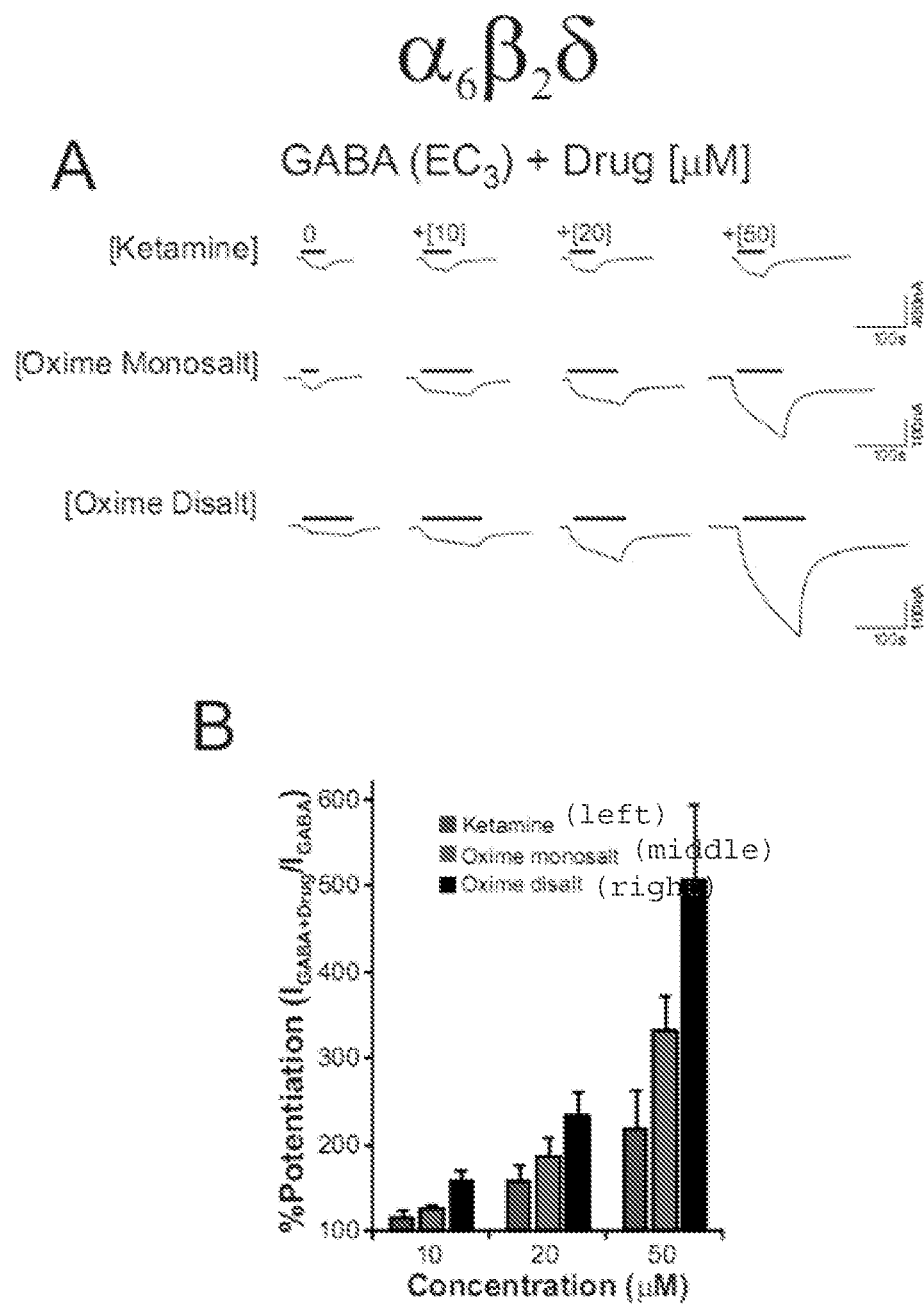
FIGS. 14A and 14B potentiation of GABA current at clinically relevant concentrations illustrate GABA receptor potentiation comparing ketamine to the mono and disalt of the ketamine oxime derivative.
Figure 15:
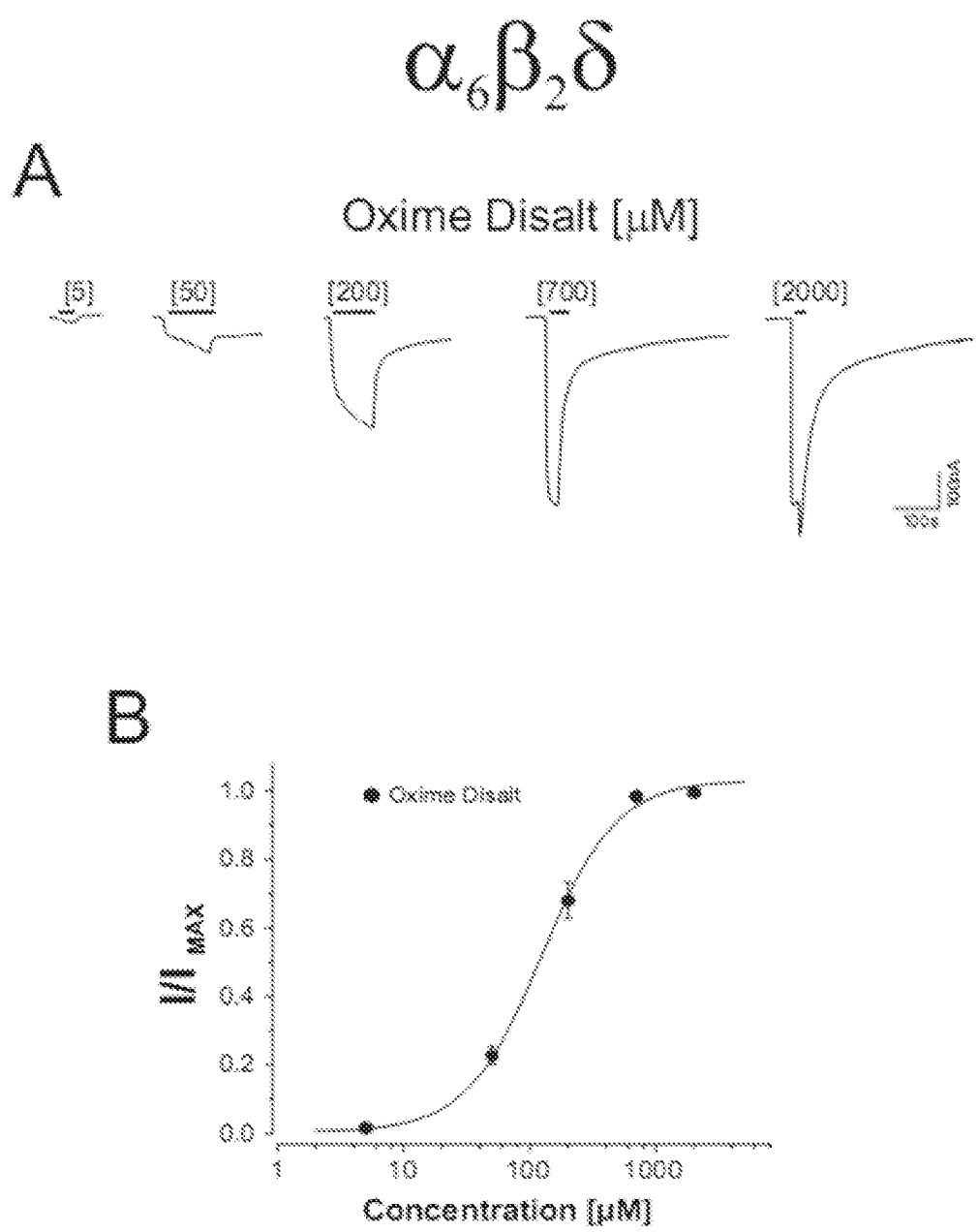
FIG. 15A illustrates the drug effects on GABA evoked currents at alpha 6 beta 2 delta receptors.
FIG. 15B illustrates the GABA current potentiation as a function of concentration.

The ketamine analogues were tested for agonist activities at GABAa receptors both in the presence and absence of GABA (FIGS. 13-16). The ketamine analogues acted as an agonist of GABAa receptors and potentiated GABA induced currents. This data is shown in Table 2. Oxime 2 was prepared both as a mono-salt and di-salt. Oxime 2 in both forms greatly potentiated the GABA$_A$ current relative to ketamine at various concentrations (FIG. 13). On α6β2δ subtype receptors, Oxime 2 disalt has shown greater potentiation at 20 μM concentration. Even on α1β2γ2 receptors, Oxime 2 disalt greatly potentiated GABA$_a$ current at 20 μM when ketamine is not able to potentiate any current. The oxime disalt showed nearly two fold increase in potentiation at 50 μM concentration on α6β2δ subtype receptor and similarly on α1β2γ2 receptors at 100 μM concentration.

FIGS. 14A and 14B illustrate GABA receptor potentiation comparing ketamine to the mono and disalt of the ketamine oxime derivative. FIG. 21A illustrates the drug effects on GABA evoked currents at alpha 6 beta 2 delta receptors. FIG. 21B illustrates the GABA current potentiation as a function of concentration.

FIG. 15A illustrates the drug effects on GABA evoked currents at alpha 6 beta 2 delta receptors. FIG. 15B illustrates the GABA current potentiation as a function of concentration.

Figure 16:
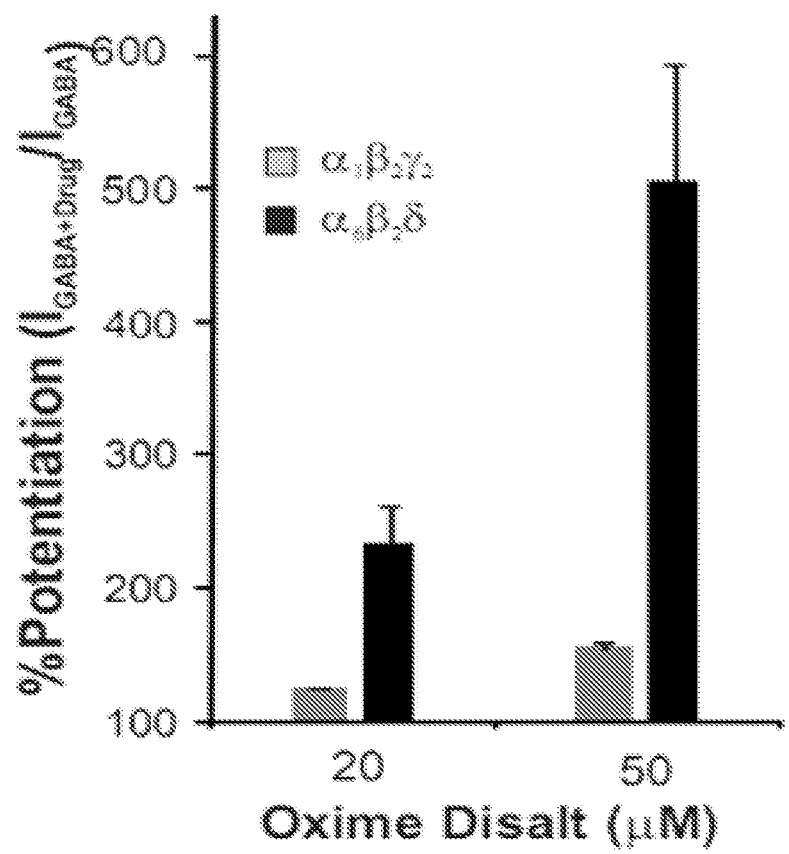
FIG. 16 illustrates the oxime disalt potentiation of GABA induced activation of both types of GABAa receptors.

FIG. 16 illustrates the oxime disalt potentiation of GABA induced activation of both types of GABAa receptors.

Methoxime 3 and benzoxime 4 analogues did not evoke considerable response from GABAa receptors. Semicarbazone 5 was also been less sensitive than ketamine towards receptors potentiating GABA$_A$ current. Hydroxy analogue 6 has shown less sensitivity than ketamine towards both GABA$_a$ receptors. This could be seen even at higher concentrations like 100 μM (Table 2).

From this analysis, bulkier groups like methoxime and benzoxime are less effective in potentiation of GABAa receptors. Among polar groups, bulkier groups like the one in semicarbazone 5 and smaller groups like hydroxyl were also insensitive towards GABA$_a$ receptors. It indicates that the double bond and the presence of small polar groups as in oxime 2 are crucial to potentiate. The increased potentiation can be attributed to the reduced lipophilicity of oxime 2 compared to ketamine.

Example 3

Antagonist Activities of Ketamine Analogues on NMDA Receptors

Figure 17:
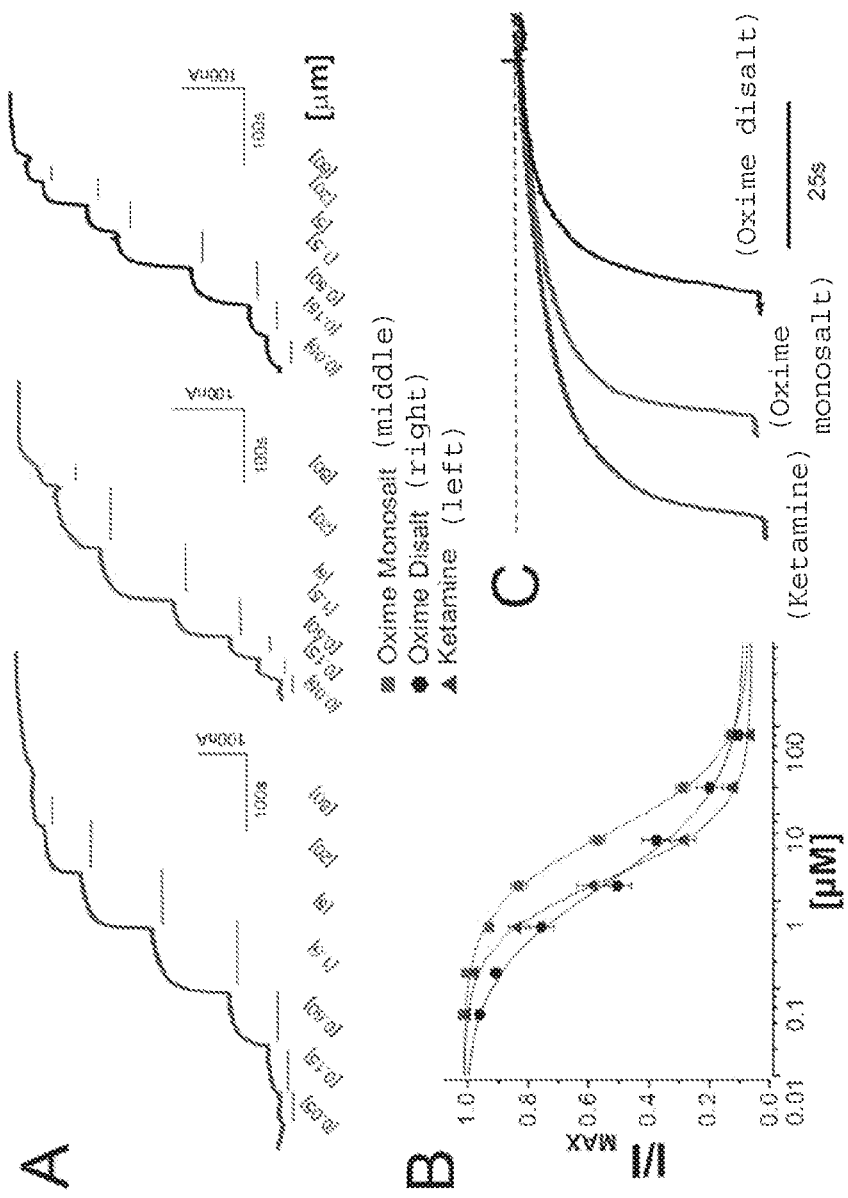
FIGS. 17A to 17C illustrate graphs of NMDA receptor blockade comparing ketamine to the mono and disalt of the ketamine oxime derivative. Activity at NR1/NR2A receptors: IC50 values are comparable for all three compounds at approximately 1 μm. However, as indicated in FIG. 17C, the on-off rate is much higher for the oximes.
Figure 18:
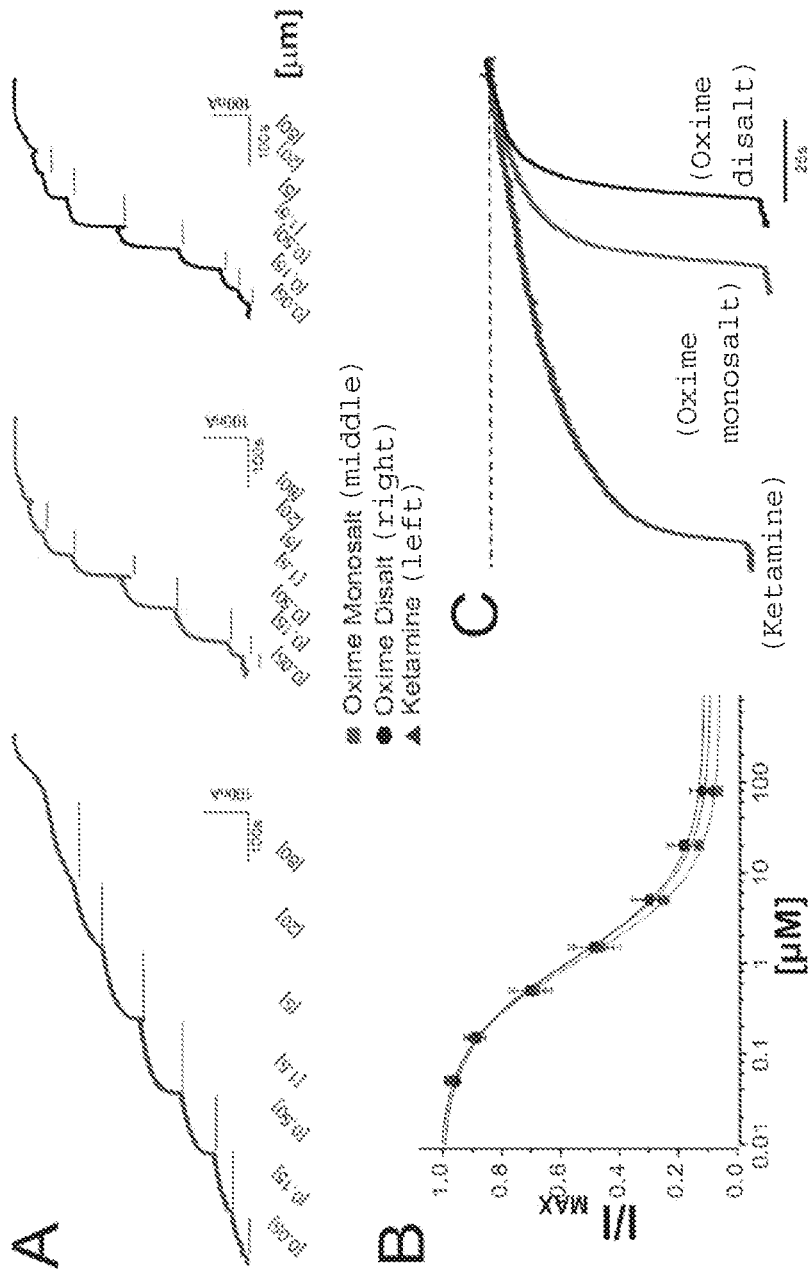
FIGS. 18A to 18C illustrate graphs of NMDA receptor blockade comparing ketamine to the mono and disalt of the ketamine oxime derivative. Activity at NR1/NR2B receptors: IC50 values are comparable for all three compounds at approximately 1 μm. However, as indicated in FIG. 18C, the on-off rate is much higher for the oximes.
Figure 19:
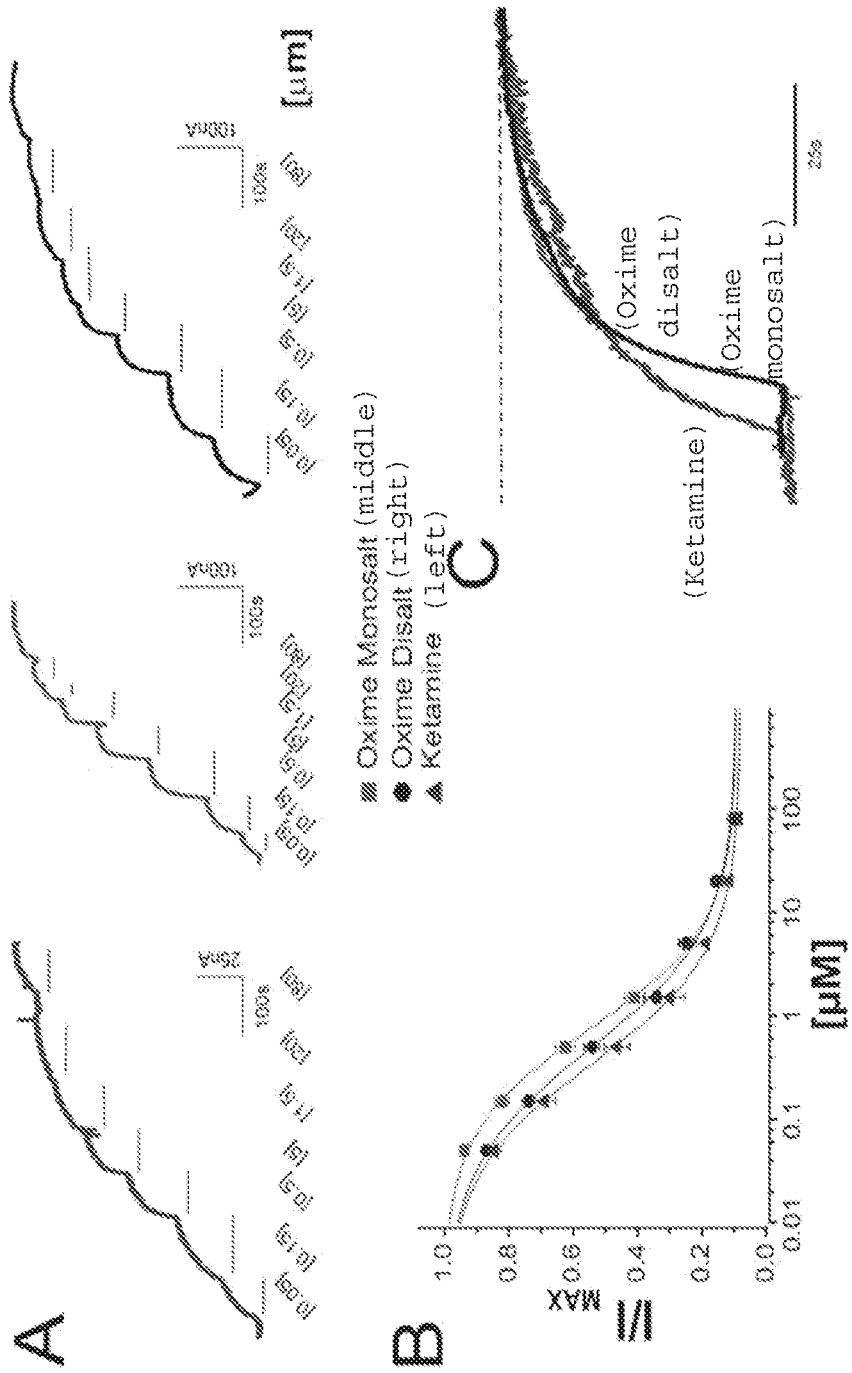
FIGS. 19A to 19C illustrate graphs of NMDA receptor blockade comparing ketamine to the mono and disalt of the ketamine oxime derivative. Activity at NR1/NR2C receptors: IC50 values are comparable for all three compounds at approximately 1 μm. However, as indicated in FIG. 19C, the on-off rate is much higher for the oximes.
Figure 20:
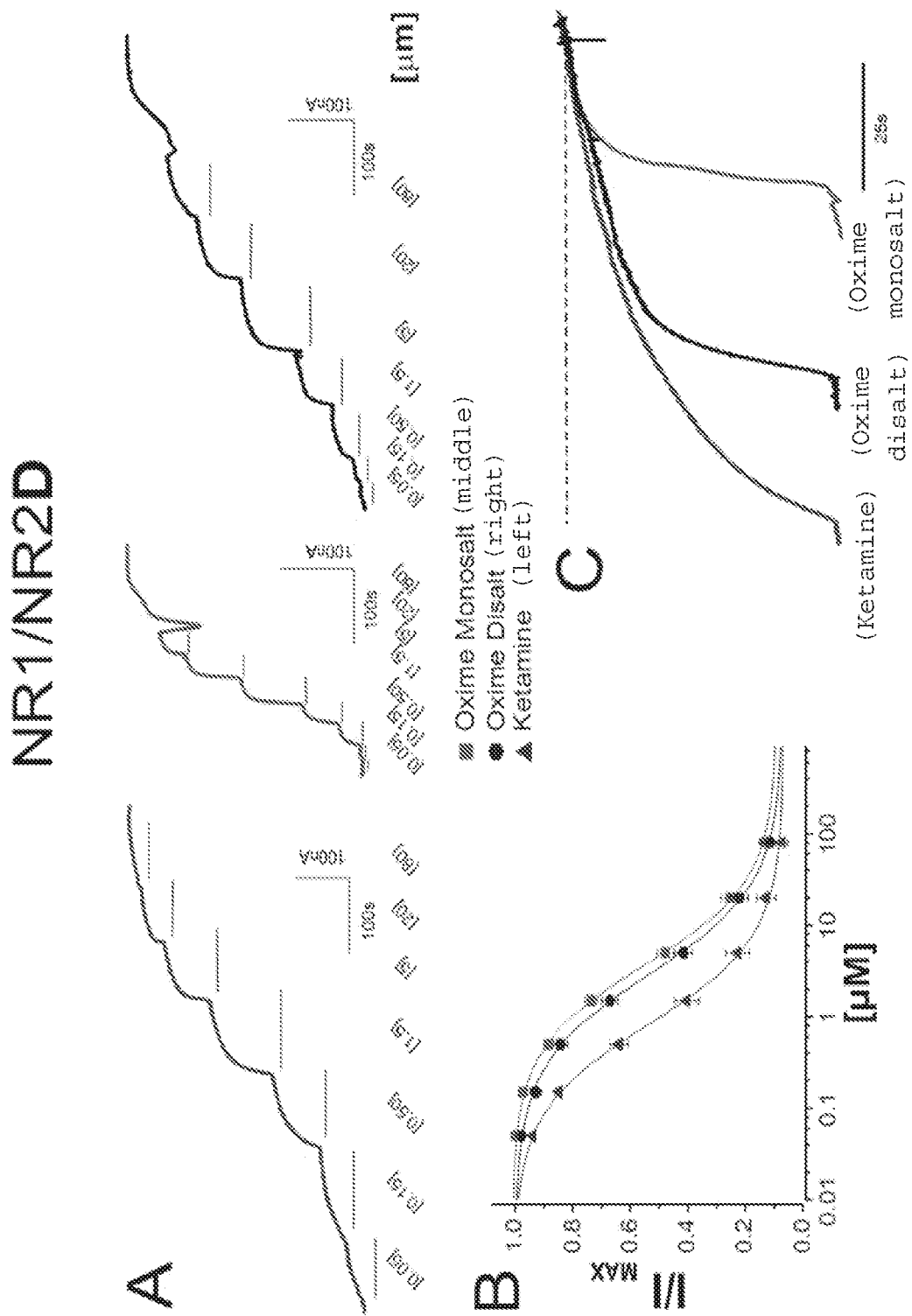
FIGS. 20A to 20C illustrate graphs of NMDA receptor blockade comparing ketamine to the mono and disalt of the ketamine oxime derivative. Activity at NR1/NR2D receptors: IC50 values are comparable for all three compounds at approximately 1 μm. However, as indicated in FIG. 20C, the on-off rate is much higher for the oximes.

Initially, the new ketamine analogues synthesized were tested at 50 μM concentration against three different NMDA receptors (Table 3 and FIGS. 17, 18, and 20) for their antagonist activity. Modification of the carbonyl group in ketamine to oxime has increased inhibition at NMDA-A and -B receptors while the comparable activity can be observed at NMDA-D receptors (Table 3). Particularly it had a greater inhibition at NMDA-A receptors than ketamine and similar to PCP. It even had a similar inhibition at NMDA-B and -D receptors. This could establish the fact that oxime 2 is target specific towards NMDA-A receptors at 50 μM concentration. Replacement of the carbonyl group in ketamine with other analogues like methoxime, benzoxime and semicarbazone has resulted decreased effect on all receptors (Table 3). % Recovery of current measured post drug treatment to reflect anesthetically effectiveness of drug has also shown that oxime 2 retains similar effect on A and B receptors while showing ineffectiveness at D receptors compared to ketamine. Oxime 2 also shown comparable activity with PCP (Phencyclidine) at NMDA-A and -D receptors in inhibition. At NMDA-B and -D receptors, it shown greater affinity than PCP as obvious from % recovery of current measured at these receptors (Table 3).

TABLE 3

Antagonist activities of ketamine analogues on NMDA receptors.[a,b,c]

| | NMDA-A (NR1/2A) | | NMDA-B (NR1/2B) | | NMDA-D (NR1/2D) | |
|---|---|---|---|---|---|---|
| Compound | % Inhibition | % Recovery | % Inhibition | % Recovery | % Inhibition | % Recovery |
| Ketamine | 57.627 | 84.745 | 80.512 | 34.564 | 88.09 | 26.19 |
| Oxime | 89.23 | 86.1538 | 83.0188 | 33.9622 | 86.666 | 52.272 |
| Methoxime | 25.257 | 98.453 | 75.597 | 71.6417 | 57.5 | 82.5 |
| Benzoxime | — | — | 40.993 | 77.639 | 49.315 | 79.452 |
| Semicarbazone | 33.557 | — | 50.757 | 98.484 | 33.3333 | — |
| PCP | 88.372 | 93.953 | 96.774 | 59.677 | 87.5 | 66.666 |

[a]= % Inhibition = $(I_{Glu/Gly} - I_{Drug}/I_{Glu/Gly})$ 100.
[b]= % Recovery = $(I_{Post\ treatment} - I_{Glu/Gly})$ 100.
[c]= Drug concentration is 50 μM at receptor.

Thus encouraged by this result, oxime 2 affinity studies have been conducted at various concentrations to determine IC$_{50}$ values (Table 4). The % recovery reflects long lasting effect of drug as anesthetic to determine anesthetically relevant concentration. Though oxime 2 showed greater or similar inhibition at 50 μM concentration with ketamine at all NMDA receptors, it's affinity was attenuated over a range of concentrations from 0.1 to 200 μM in terms of % recovery of response (Table 4 and FIG. 17-20) by observing IC$_{50}$ values.

FIGS. 17A to 17C illustrate graphs of NMDA receptor blockade comparing ketamine to the mono and disalt of the ketamine oxime derivative. Activity at NR1/NR2A receptors: IC50 values are comparable for all three compounds at approximately 1 μm. However, as indicated in FIG. 17C, the on-off rate is much higher for the oximes.

FIGS. 18A to 18C illustrate graphs of NMDA receptor blockade comparing ketamine to the mono and disalt of the ketamine oxime derivative. Activity at NR1/NR2B receptors: IC50 values are comparable for all three compounds at approximately 1 μm. However, as indicated in FIG. 18C, the on-off rate is much higher for the oximes.

FIGS. 19A to 19C illustrate graphs of NMDA receptor blockade comparing ketamine to the mono and disalt of the ketamine oxime derivative. Activity at NR1/NR2C receptors: IC50 values are comparable for all three compounds at approximately 1 μm. However, as indicated in FIG. 19C, the on-off rate is much higher for the oximes.

FIGS. 20A to 20C illustrate graphs of NMDA receptor blockade comparing ketamine to the mono and disalt of the ketamine oxime derivative. Activity at NR1/NR2D receptors: IC50 values are comparable for all three compounds at approximately 1 μm. However, as indicated in FIG. 20C, the on-off rate is much higher for the oximes.

FIG. 25 is a Table showing the tabulation of IC50 values for the action of the drugs at NMDA receptor subtypes.

TABLE 4

Affinity studies of ketamine and oxime against NMDA receptors with $IC_{50}$ values.

| NMDA Receptor | % Recovery (Ketamine) | % Recovery (Oxime) | $IC_{50}$ (Ketamine) | $IC_{50}$ (Oxime) |
|---|---|---|---|---|
| NMDA-NR1/2A | 28 | 74 | 2.32 | 5.911 |
| NMDA-NR1/2B | 19 | 31 | 0.82 | 1.068 |
| NMDA-NR1/2C | — | 44 | — | 0.747 |
| NMDA-NR1/2D | 24 | 68 | 0.76 | 1.068 |

Figure 21:
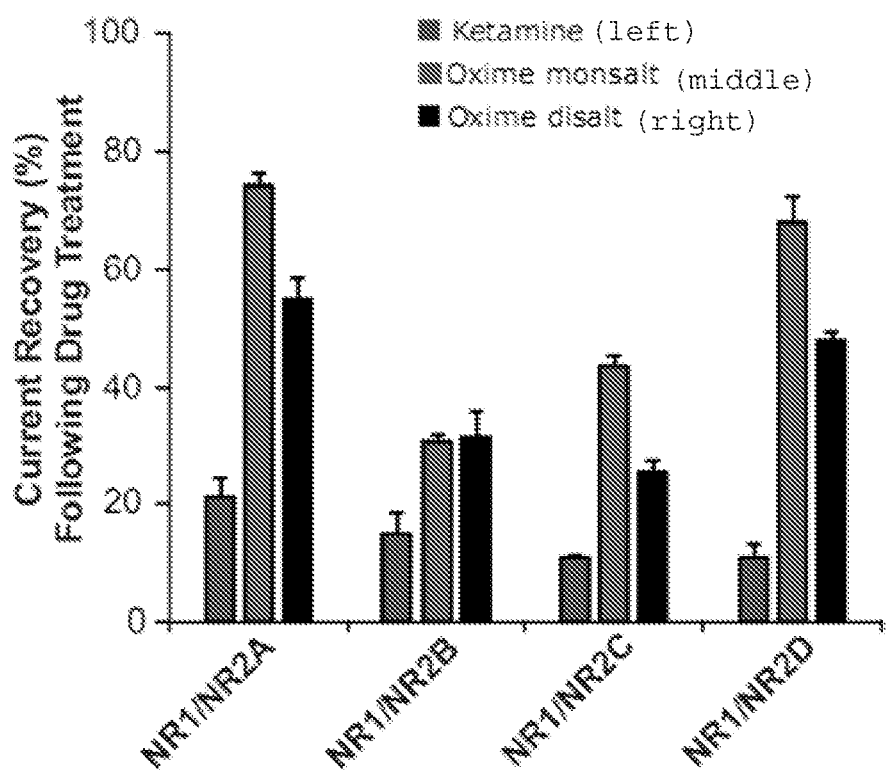
FIG. 21 illustrates a graph showing NMDA receptor blockade recovery, comparing ketamine to the mono and disalt of the ketamine oxime derivative. Data indicates much faster off rate of the oximes from the NMDA receptors.

FIG. 21 illustrates a graph showing NMDA receptor blockade recovery, comparing ketamine to the mono and disalt of the ketamine oxime derivative. Data indicates much faster off rate of the oximes from the NMDA receptors.

Recovery is much less for ketamine compared to the oxime which means that ketamine has longer lasting effects and higher affinity. The oxime shown similar inhibition to ketamine at NMDA-B, C, D receptors, but the oxime has two fold higher $IC_{50}$ values versus ketamine at NMDA-A receptors.

Conclusions

Modification of carbonyl group in ketamine to oxime, methoxime, benzoxime, semicarbazone and hydroxyl groups has provided an insight into the effect of size of the groups towards $GABA_a$ receptors. Oxime has shown to reduce lipophilicity, while methoxime, benzoxime shown increased lipophilicity. This study has also shown that polar groups like semicarbazone and hydroxyl were not able to increase the potency towards $GABA_a$ receptors. Thus oxime 2 has been better agonist at $GABA_a$ receptors exhibiting two times more excitory post synaptic potential than ketamine. From this study, though anesthetic efficacy of ketamine and PCP (Phencyclidine) as non-competitive inhibitors of NMDA (N-Methyl-D-Aspartate) led to classifying them as dissociate anesthetics, Oxime 2 has shown improved or similar potency towards various NMDA receptors. This could be beneficial to study further anesthetic efficacy of oxime 2 in epileptic seizures, other convulsant side effects which are associated with ketamine. Ketamine is known to be more effective anesthetic across different animal species but in humans it is associated with various adverse effects like inducing catalepsy at higher doses and hallucinations at lower doses. Since oxime has shown greater or comparable potency at lower doses as antagonist exciting postsynaptic potential at various NMDA receptors and less duration of affinity, it could be interesting to study its efficacy across various animals.

Example 4

The effect of ketamine oxime disalt on motor coordination in rats was evaluated. A dose response study was conducted and the results are listed in FIG. 22 and FIG. 23. FIG. 22 shows open field behavior for the six minute period following oxime injection at the indicated concentrations. FIG. 23 shows open field behavior for the 12 minute period following oxime injection. These data demonstrate the CNS depressant effects of the oxime on motor coordination.

Example 5

Figure 24:
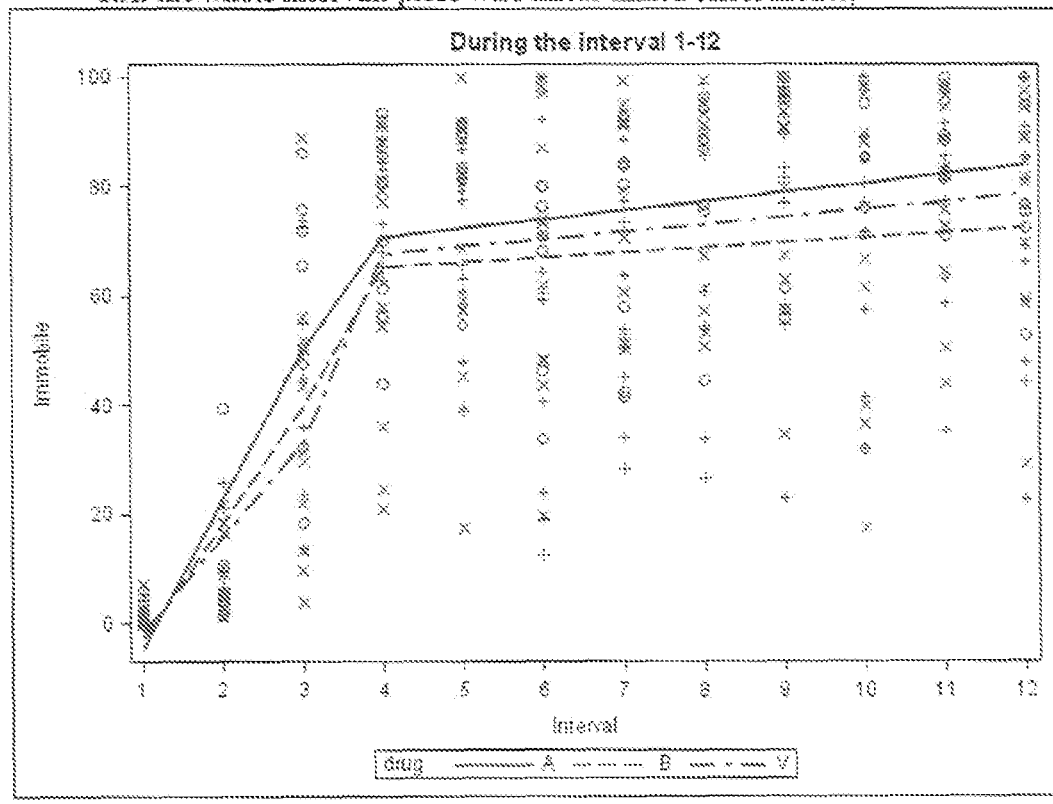
FIG. 24 illustrates an analysis of the antidepressant effects of ketamine and the oxime analogue at 5 mg/kg in rats undergoing tail suspension for 12 minutes. Note that immobility, giving up the struggle, is a sign of depression in this model. No significant differences were seen between either drug or saline overall, however, slope analysis indicated that the oxime analogue decreased immobility, and therefore has the potential to act as an antidepressant. V is vehicle, A is the oxime, B is ketamine.

Rats were dosed with ketamine oxime disalt and then tested in a model of depression. FIG. 24 illustrates an analysis of the antidepressant effects of ketamine and the oxime analogue at 5 mg/kg in rats undergoing tail suspension for 12 minutes. Note that immobility, giving up the struggle, is a sign of depression in this model. No significant differences were seen between either drug or saline overall, however, slope analysis indicated that the oxime analogue decreased immobility, and therefore has the potential to act as an antidepressant. V is vehicle, A is ketamine, B is ketamine oxime analogue.

Example 6

One or more of the analogues of the ketamine of the present disclosure may be used in treatment of phantom pain, epilepsy, and/or depression with reduced hallucinogenic effect.

Ketamine, a phencyclidine (PCP) analogue, is an intravenous anesthetic capable of inducing analgesia at low doses to anesthesia at higher doses. Ketamine was selected from over 200 PCP analogues for its relatively superior anesthetic properties and lower (psychedelic) side effects. Ketamine produces analgesia superior to opioids in patients suffering from neuropathic pain (e.g., phantom pain), and has shown great potential as an antidepressant agent. In spite of its clinical advantages, ketamine is a hallucinogenic drug of abuse. At the molecular level, both ketamine and PCP reduce excitatory input via the inhibition of NMDA receptors, yet paradoxically (considering the better quality of ketamine anesthesia), PCP shows a markedly higher affinity for this target. We have shown that in addition to blocking of the NMDA receptors, ketamine, but not PCP, increases the activity of the inhibitory ligand-gated ion channel α6β2/3δ $GABA_A$ receptor. These data suggest that the ketamine's superior anesthetic properties compared to PCP may be due to its selective actions on α6β2/3δ $GABA_A$ receptors.

Ketamine's Clinical Application and Potential

1) Intravenous anesthetic: Ketamine is a preferred induction agent in trauma patients suffering from severe bleeding and hypovolemia, as in contrast to most anesthetic agents, it increases blood pressure and heart rate. Ketamine was used extensively in battlefield of Vietnam.

2) Unique analgesic action: At one/tenth the induction dose, ketamine produces analgesia. Recent studies have demonstrated that ketamine-induced analgesia is superior to opioids in patients suffering from neuropathic and post-traumatic pain (e.g., post-amputation or phantom pain).

3) Antidepressant properties: Ketamine at low doses has shown great promise as an antidepressant agent. In recent studies, ketamine exhibited superior antidepressant effects compared to the often-prescribed SSRI (fluoxetine, Prozac®) class of drugs.

Ketamine's Untoward Effect:

In spite of its clinical advantages, ketamine is a hallucinogenic drug of abuse.

To broaden the spectrum of ketamine's anesthetic, analgesic and antidepressant action, as well as increase its margin of safety, decrease its incidence of adverse effects, and reduce its potential as a drug of abuse, we synthesized several ketamine analogues and tested their action for increasing the activity of α6β2/3δ $GABA_A$ receptors and for blocking NMDA receptors subtypes (Scheme 6). One of the ketamine analogues, an oxime variant (Scheme 6 VII), exhibited increasing action on α6β2/3δ $GABA_A$ receptor activity while retaining the blocking effect on the NMDA receptors when compared to ketamine. Although the oxime's blocking action on the NMDA receptor subtypes was similar to ketamine in terms of potency (IC50), its lasting effect following wash of the drug (ability to retain its blocking effect following wash of the drug; a high affinity effect) was less than ketamine. Oxime disalt was tested in vivo on rats and, in summary, produced a loss of equilibrium, unsteady gait and immobility at higher doses without loss of righting reflex (an indication of anesthesia). The oxime compounds may have therapeutic potential for pain, muscle relaxant, be used for analgesia, as an antidepressant, for cognitive impairment, neuropsychiatric disorders such as schizophrenia, and epilepsy.

not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement technique and/or the numerical value. In addition, the phrase "about 'x' to 'y'" includes "about 'x' to about 'y'".

Many variations and modifications may be made to the above-described embodiments. All such modifications and

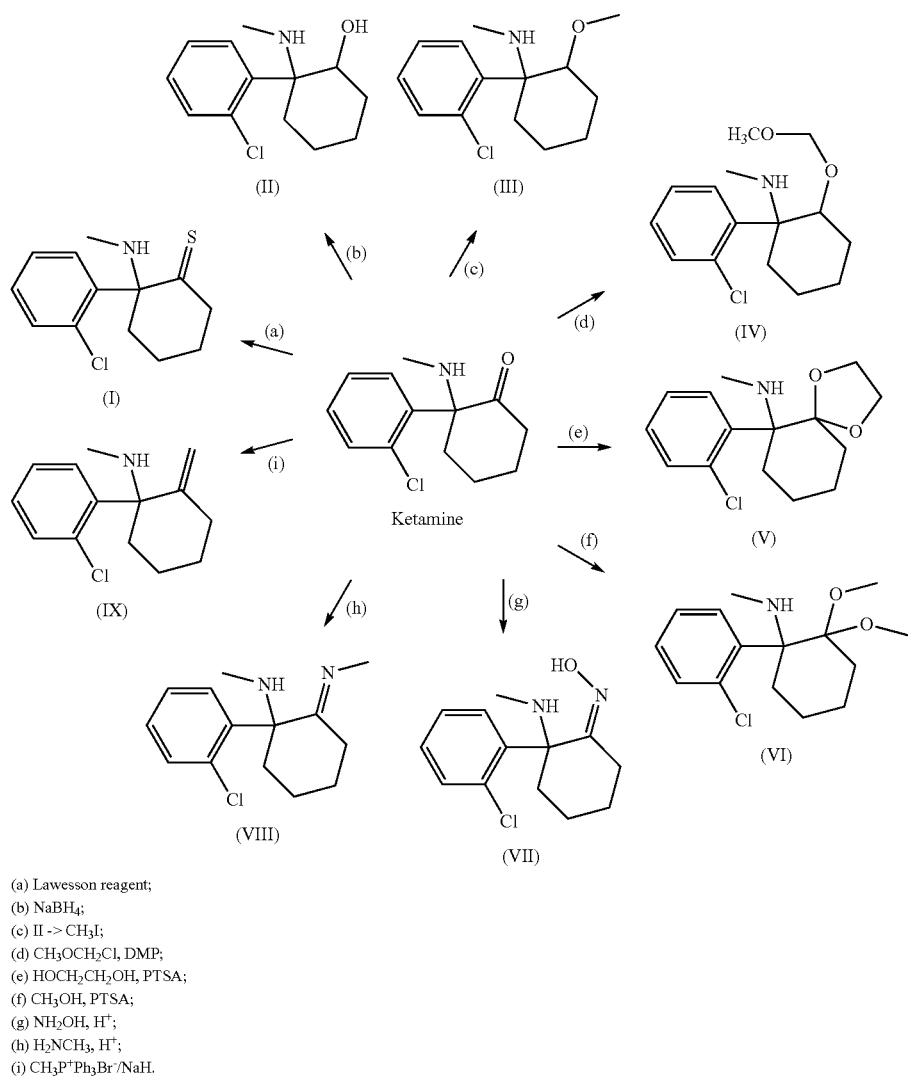

Scheme 6. Ketamine analogues for a to i. Scheme - Synthesis of Ketamine analogues at the carbonyl carbon (a) Lawesson reagent;
(b) NaBH$_4$;
(c) II -> CH$_3$I;
(d) CH$_3$OCH$_2$Cl, DMP;
(e) HOCH$_2$CH$_2$OH, PTSA;
(f) CH$_3$OH, PTSA;
(g) NH$_2$OH, H$^+$;
(h) H$_2$NCH$_3$, H$^+$;
(i) CH$_3$P$^+$Ph$_3$Br$^-$/NaH.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include variations are intended to be included herein within the scope of this disclosure and protected by the following claims.

REFERENCES, EACH OF WHICH IS INCORPORATED HEREIN BY REFERENCE (1). Bormann, J. *Trends in Neurosciences* 1988, 11, 112.

(2). Bormann, J. *Trends in Pharmacological Sciences* 2000, 21, 16.

(3). Sivilotti, L.; Nistri, A. *Progress in Neurobiology* 1991, 36, 35.

(4). Simon, J.; Wakimoto, H.; Fujita, N.; Lalande, M.; Barnard, E. A. *j biol. chem.* 2004, 279, 41422.

(5). Sieghart, W. *Pharmacol. Rev.* 1995, 47, 181.

(6). (a). Stephenson, F. A. *Biochemical Journal* 1995, 310 (Pt 1), 1. (b). McKernan, R. M.; Whiting, P. J. *Trends in Neurosciences* 1996, 19, 139. (c). Farrar, S. J.; Whiting, P. J.; Bonnert, T. P.; McKernan, R. M. *j biol. chem.* 1999, 274, 10100.

(7). (a). Wisden, W.; Korpi, E. R.; Bahn, S. *Neuropharmacology* 1996, 35, 1139. (b). Laurie, D. J.; Wisden, W.; Seeburg, P. H. *Journal of Neuroscience* 1992, 12, 4151.

(8). Tyrrell, T.; Willshaw, D. *Philos Trans R Soc Lond B Biol Sci* 1992, 336, 239.

(9). Feigenspan, A.; Bormann, J. *Prog Retin Eye Res* 1998, 17, 99.

(10). Gupta, S. P. *Prog Drug Res* 1995, 45, 67.

(11). Olsen, R. W. *Journal of Neurochemistry* 1981, 37, 1.

(12). Newland, C. F.; Cull-Candy, S. G. *J Physiol* 1992, 447, 191.

(13). Barberis, A.; Cherubini, E.; Mozrzymas, J. W. *Journal of Neuroscience* 2000, 20, 8618.

(14). Wingrove, P. B.; Wafford, K. A.; Bain, C.; Whiting, P. J. *Proc Natl Acad Sci USA* 1994, 91, 4569.

(15). Yang, C. X.; Xu, H.; Zhou, K. Q.; Wang, M. Y.; Xu, T. L. *Anesthesia and Analgesia* 2006, 102, 1114.

(16). (a) Orser, B. A.; Wang, L. Y.; Pennefather, P. S.; MacDonald, J. F. *Journal of Neuroscience* 1994, 14, 7747 (b) Ham, M.; Kai, Y.; Ikemoto, Y. *Anesthesiology* 1993, 79, 781.

(17). Tomlin, S. L.; Jenkins, A.; Lieb, W. R.; Franks, N. P. *Anesthesiology* 1998, 88, 708.

(18). Kohr, G. *Cell and Tissue Research* 2006, 326, 439.

(19). Mayer, M. L.; Westbrook, G. L.; Guthrie, P. B. *Nature* 1984, 309, 261.

(20). Li, F.; Tsien, J. Z. *N Engl J Med* 2009, 361, 302.

(21). Mayer, M. L. *Nature* 2006, 440, 456.

(22). (a). Park, C. K.; Nehls, D. G.; Graham, D. I.; Teasdale, G. M.; Mcculloch, J. *Annals of Neurology* 1988, 24, 543. (b). Dirnagl, U.; Iadecola, C.; Moskowitz, M. A. *Trends in Neurosciences* 1999, 22, 391. (c). Whetsell, W. O. *Journal of Neuropathology and Experimental Neurology* 1996, 55, 1. (d). Lipton, S. A. *Current Opinion in Neurology and Neurosurgery* 1993, 6, 588. (e). Wang, C. X.; Shuaib, A. *Curr Drug Targets CNS Neurol Disord* 2005, 4, 143.

(23). (a). Vicini, S.; Wang, J. F.; Li, J. H.; Zhu, W. J.; Wang, Y. H.; Luo, J. A. H.; Wolfe, B. B.; Grayson, D. R. *Journal of Neurophysiology* 1998, 79, 555. (b). Yuan, H. J.; Hansen, K. B.; Vance, K. M.; Ogden, K. K.; Traynelis, S. F. *Journal of Neuroscience.* 2009, 29, 12045. (c). Neyton, J.; Paoletti, P. *Journal of Neuroscience* 2006, 26, 1331.

(24). (a). Lodge, D.; Anis, N. A. *European Journal of Pharmacology* 1982, 77, 203. (b). MacDonald, J. F.; Nowak, L. M. *Trends in Pharmacological Sciences* 1990, 11, 167. (c). MacDonald, J. F.; Miljkovic, Z.; Pennefather, P. *Journal of Neurophysiology.* 1987, 58, 251. (d). Anis, N. A.; Berry, S. C.; Burton, N. R.; Lodge, D. *British Journal of Pharmacology* 1983, 79, 565.

(25). Parsons, C. G.; Quack, G.; Bresink, I.; Baran, L.; Przegalinski, E.; Kostowski, W.; Krzascik, P.; Hartmann, S.; Danysz, W. *Neuropharmacology* 1995, 34, 1239.

(26). (a). Johnstone, M.; Evans, V.; Baigel, S. *British Journal of Anaesthesia* 1959, 31, 433. (b). Macdonald, J. F.; Bartlett, M. C.; Mody, I.; Pahapill, P.; Reynolds, J. N.; Salter, M. W.; Schneiderman, J. H.; Pennefather, P. S. *Journal of Physiology—London* 1991, 432, 483. (c). Rogawski, M. A.; Wenk, G. L. Cns *Drug Reviews* 2003, 9, 275. (d). Chen, G. *Archives Internationales De Pharmacodynamie Et De Therapie* 1965, 157, 193. (e). Chen, G.; Ensor, C. R.; Russell, D.; Bohner, B. *Journal of Pharmacology and Experimental Therapeutics* 1959, 127, 241.

(27). Mccarthy, D. A.; Chen, G.; Kaump, D. H.; Ensor, C. *Journal of New Drugs* 1965, 5, 21.

(28). Seeman, P.; Guan, H. C.; Hirbec, H. *Synapse* 2009, 63, 698.

(29). Kapur, S.; Seeman, P. *Molecular Psychiatry* 2002, 7, 837.

(30). Hirota, K.; Okawa, H.; Appadu, B. L.; Grandy, D. K.; Devi, L. A.; Lambert, D. G. *Anesthesiology* 1999, 90, 174.

(31). Hustveit, O.; Maurset, A.; Oye, I. *Pharmacology & Toxicology* 1995, 77, 355.

(32). (a). Kawano, T.; Oshita, S.; Takahashi, A.; Tsutsumi, Y.; Tanaka, K.; Tomiyama, Y.; Kitahata, H.; Nakaya, Y. *Anesthesiology* 2005, 102, 93. (b). Wagner, L. E.; Gingrich, K. J.; Kulli, J. C.; Yang, J. *Anesthesiology* 2001, 95, 1406.

(33). (a). Kress, H. G. *Anaesthesist* 1997, 46, S8. (b). Hevers, W.; Luddens, H. *Neuropharmacology* 2002, 42, 34. (c). Hevers, W.; Luddens, H. *Molecular Neurobiology* 1998, 18, 35.

(34). (a). Adler, C. M.; Malhotra, A. K.; Elman, I.; Goldberg, T.; Egan, M.; Pickar, D.; Breier, A. *American Journal of Psychiatry* 1999, 156, 1646. (b). Morgan, C. J.; Mofeez, A.; Brandner, B.; Bromley, L.; Curran, H. V. *Neuropsychopharmacology* 2004, 29, 208. (c). Morgan, C. J.; Mofeez, A.; Brandner, B.; Bromley, L.; Curran, H. V. *Psychopharmacology (Berl)* 2004, 172, 298. (d). Krystal, J. H.; Karper, L. P.; Seibyl, J. P.; Freeman, G. K.; Delaney, R.; Bremner, J. D.; Heninger, G. R.; Bowers, M. B., Jr.; Charney, D. S. *Arch Gen Psychiatry* 1994, 51, 199.

(35). (a). Olney, J. W.; Labruyere, J.; Wang, G.; Wozniak, D. F.; Price, M. T.; Sesma, M. A. *Science* 1991, 254, 1515. (b). Seamans, J. *Nature Chemical Biology* 2008, 4, 91.

(36). (a). Hota, D.; Bansal, V.; Pattanaik, S. *Methods Find Exp Clin Pharmacol* 2007, 29, 443. (b). Mathew, S. J.; Manji, H. K.; Charney, D. S. *Neuropsychopharmacology.* 2008, 33, 2080. (c). Krystal, J. H. *Swiss Med Wkly* 2007, 137, 215.

(37). (a). Avila, M. T.; Weiler, M. A.; Lahti, A. C.; Tamminga, C. A.; Thaker, G. K. *Am J Psychiatry* 2002, 159, 1490. (b). Radant, A. D.; Bowdle, T. A.; Cowley, D. S.; Kharasch, E. D.; Roy-Byrne, P. P. *Neuropsychopharmacology* 1998, 19, 434. (c). Bowdle, T. A.; Radant, A. D.; Cowley, D. S.; Kharasch, E. D.; Strassman, R. J.; Roy-Byrne, P. P. *Anesthesiology* 1998, 88, 82. (d). Petit, L.; Clark, V. P.; Ingeholm, J.; Haxby, J. V. *Journal of Neurophysiology* 1997, 77, 3386. (e). Braff, D. L.; Geyer, M. A.; Light, G. A.; Sprock, J.; Perry, W.; Cadenhead, K. S.; Swerdlow, N. R. *Schizophrenia Research* 2001, 49, 171.

(38). (a). Burak, K.; Lipnicka, U.; Orszanska, H.; Rykowski, Z.; Witkiewicz, K.; Wrzesien, J.; Bogdal, M.; Krzywasinski, L.; Borkowska, B. *Farmaco Sci.* 1985, 40, 285. (b). Yang, D. J.; Davisson, J. N. *J. MED. CHEM.* 1985, 28, 1361. (c). Cone, E. J.; McQuinn, R. L.; Shannon, H. E. J. *Pharm. and Exp. Ther.* 1984, 228, 147.

(39). Zarantonello, P.; Bettini, E.; Paio, A.; Simoncelli, C.; Terreni, S.; Cardullo, F. *Bioorg. & Med. Chem. Lett.* 2011, 21, 2059.

(40). Hevers, W.; Hadley, S. H.; Luddens, H.; Amin, J. *J. Neurosci.* 2008, 28, 5383.

We claim:

1. A composition, comprising: a ketamine analogue having one of the following structures:

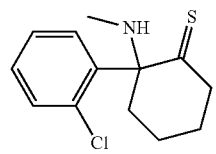 (I)

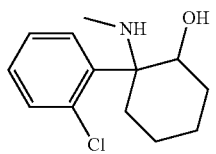 (II)

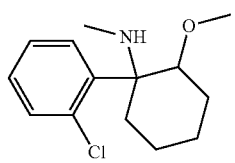 (III)

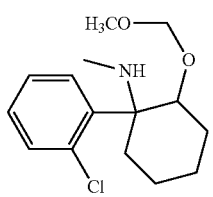 (IV)

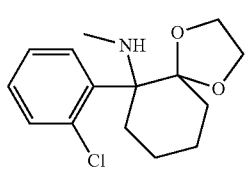 (V)

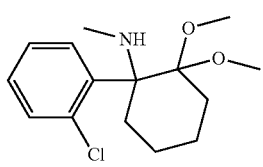 (VI)

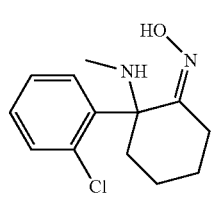 (VII)

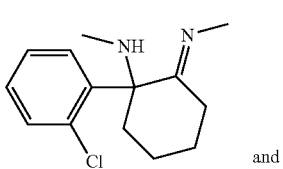 (VIII) and

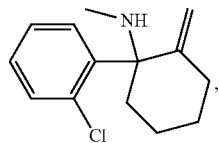 (IX)

a salt thereof, or a disalt thereof.

2. The composition of claim 1, wherein the ketamine analogue has the following structure:

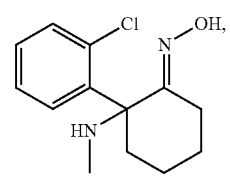

a salt thereof, or a disalt thereof.

3. The composition of claim 2, wherein the salt is a chloride salt at the primary amine.

4. The composition of claim 2, wherein the salt is a chloride disalt at the primary amine and the imine.

5. A pharmaceutical composition comprising: a therapeutically effective amount of a ketamine analogue having one the following structures:

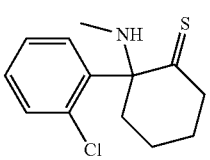 (I)

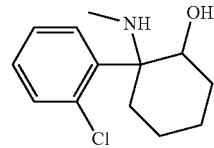 (II)

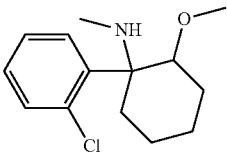 (III)

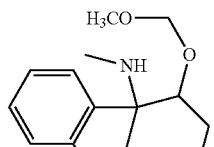 (IV)

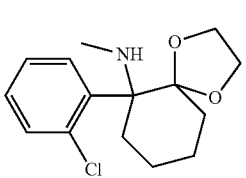 (V)

(VI) 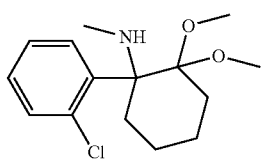

(VII) 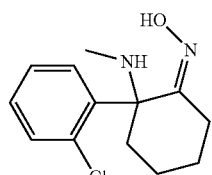

(VIII) 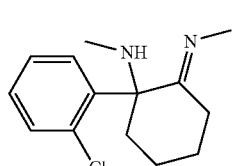

(IX) 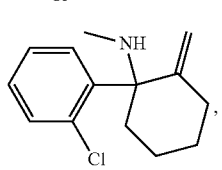

a pharmaceutically acceptable salt thereof, or a pharmaceutically acceptable disalt thereof, and a pharmaceutically acceptable carrier, to treat a condition selected from the group consisting of neuropathic pain, depression, and epilepsy.

6. The pharmaceutical composition of claim 5, wherein the ketamine analogue has the following structure:

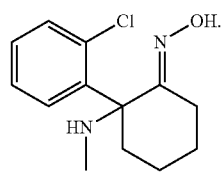 [SMILES: CNC1(c2ccccc2Cl)CCCC/C1=N\O]

7. The pharmaceutical composition of claim 6, wherein the pharmaceutically acceptable salt is a chloride salt at the primary amine.

8. The pharmaceutical composition of claim 6, wherein the pharmaceutically acceptable disalt is a dichloride salt at the primary amine and the imine.

9. A method of treating a condition comprising: delivering to a subject in need thereof, a pharmaceutical composition, wherein the pharmaceutical composition includes a therapeutically effective amount of a ketamine analogue having one of the following structures:

(I) 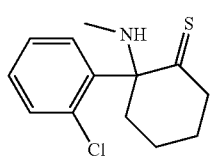

(II) 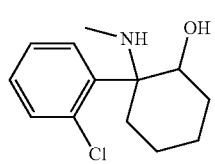

(III) 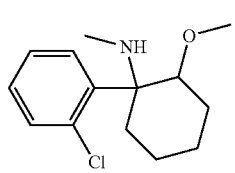

(IV) 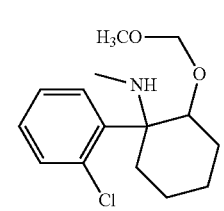

(V) 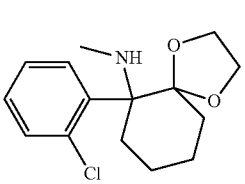

(VI) 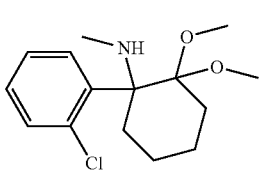

(VII) 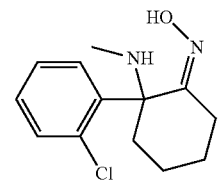

(VIII) 

and (IX) 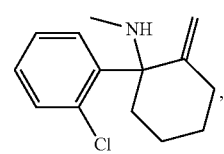

a pharmaceutically acceptable salt thereof, or a pharmaceutically acceptable disalt thereof, and a pharmaceutically acceptable carrier, to treat a condition selected from the group consisting of neuropathic pain, depression, and epilepsy.

10. The method of claim 9, wherein the ketamine analogue has the following structure:

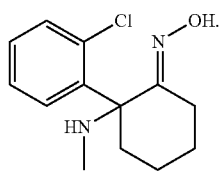 [SMILES: CNC1(c2ccccc2Cl)CCCC/C1=N\O]

11. The method of claim 9, wherein the pharmaceutically acceptable salt is a chloride salt at the primary amine.

12. The method of claim 9, wherein the pharmaceutically acceptable disalt is a dichloride salt at the primary amine and the imine.

13. The method of claim 9, wherein the ketamine analogue has the following structure:

(I)

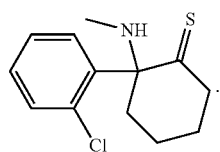

14. The method of claim 9, wherein the ketamine analogue has the following structure:

(II)

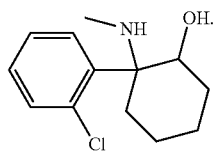

15. The method of claim 9, wherein the ketamine analogue has the following structure:

(III)

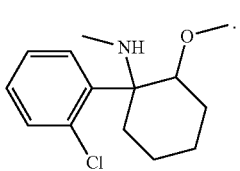

16. The method of claim 9, wherein the ketamine analogue has the following structure:

(IV)

17. The method of claim 9, wherein the ketamine analogue has the following structure:

(V)

18. The method of claim 9, wherein the ketamine analogue has the following structure:

(VI)

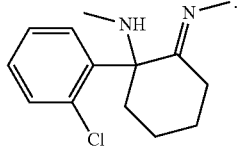

19. The method of claim 9, wherein the ketamine analogue has the following structure:

(VIII)

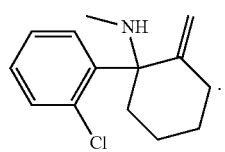

20. The method of claim 9, wherein the ketamine analogue has the following structure:

(IX)

* * * * *